(12) United States Patent
Bydder et al.

(10) Patent No.: US 12,710,499 B2
(45) Date of Patent: Aug. 18, 2026

(54) MRI CONTRAST USING SYNTHETIC PULSE SEQUENCES

(71) Applicants: Mark Bydder, Los Angeles, CA (US); Graeme Mervyn Bydder, Hale (GB)

(72) Inventors: Mark Bydder, Los Angeles, CA (US); Graeme Mervyn Bydder, Hale (GB)

( * ) Notice: Subject to any disclaimer, the term of this patent is extended or adjusted under 35 U.S.C. 154(b) by 0 days.

(21) Appl. No.: 18/898,035

(22) Filed: Sep. 26, 2024

(65) Prior Publication Data

US 2025/0110193 A1 Apr. 3, 2025

Related U.S. Application Data

(60) Provisional application No. 63/585,740, filed on Sep. 27, 2023.

(51) Int. Cl.
*G01R 33/56* (2006.01)
*A61B 5/055* (2006.01)
*G01R 33/50* (2006.01)

(52) U.S. Cl.
CPC .......... *G01R 33/5602* (2013.01); *A61B 5/055* (2013.01); *G01R 33/50* (2013.01); *G01R 33/5608* (2013.01)

(58) Field of Classification Search
CPC .......................... G01R 33/5602; G01R 33/50; G01R 33/5608; A61B 5/055
See application file for complete search history.

(56) References Cited

PUBLICATIONS

Ma., Y., et al. "Improving the understanding and performance of clinical MRI using tissue property filters and the central contrast theorem, MASDIR pulse sequences and synergistic contrast MRI," Quant Imaging Med Surg. vol. 12(9), 2022. p. 4658-4690 (Year: 2022).*

Young, I., et al., "Pulse sequences as tissue property filter (TP-filters): a way of understanding the signal, contrast and weighting of magnetic resonance images," Quant Imaging Med Surg. vol. 10(5), 2020. p. 1080-1120 (Year: 2020).*

(Continued)

*Primary Examiner* — Sean A Frith
(74) *Attorney, Agent, or Firm* — Schwegman Lundberg & Woessner, P.A.

(57) ABSTRACT

Methods include generating ultra-high contrast magnetic resonance images using synthetic pulse sequences. The techniques employ multiplied, added, subtracted and/or divided (MASDIR) inversion recovery sequences, particularly divided subtracted inversion recovery (dSIR) and divided reverse subtracted inversion recovery (drSIR) sequences. These sequences allow synthesis of narrower middle domain images from wider domain acquisitions and creation of synthetic images from tissue property maps. The methods produce increased image contrast that can reveal subtle abnormalities not visible on conventional MRI. Key aspects include using T1-bipolar filters to target specific tissues and small changes in T1, combining different tissue property filters for synergistic contrast, and quantitative T1 mapping. Clinical applications are described for detecting disease in normal-appearing tissues. The techniques enable order-of-magnitude increases in contrast compared to conventional sequences, allowing visualization of previously imperceptible changes in relaxation times.

16 Claims, 27 Drawing Sheets

(56) References Cited

PUBLICATIONS

Ma, Y., et al., “Use of Multiplied, Added, Subtracted and/or FiTted Inversion Recovery (MASTIR) pulse sequences,” Quant Imaging Med Surg. vol. 10(6), 2020. p. 1334-1369 (Year: 2020).*

Ma., Y., et al. “New options for increasing the sensitivity, specificity and scope of synergistic contrast magnetic resonance imaging (scMRI) using Multiplied, Added, Subtracted and/or FiTted (MASTIR) pulse sequences,” Quant Imaging Med Surg. vol. 10(10), 2020. p. 2030-2065 (Year: 2020).*

Beaumont, J., et al., “Avoiding Data Loss: Synthetic MRIs Generated from Diffusion Imaging Can Replace Corrupted Structural Acquisitions for Freesurfer-Seeded Tractography,” bioRxiv. 2021. p. 1-23 (Year: 2021).*

Ma, Y., et al., “Targeted magnetic resonance imaging (tMRI) of small changes in the T1 and spatial properties of normal or near normal appearing white and gray matter in disease of the brain,” Quantitative Imaging in Medicine and Surgery. vol. 13(10), 2023. p. 7304-7337. (Year: 2023).*

Ma, Ya-Jun, et al., “Improving the understanding and performance of clinical MRI using tissue property filters and the central contrast theorem, MASDIR pulse sequences and synergistic contrast MRI”, Quantitative Imaging in Medicine and Surgery 12.9, (2022), 4658-4690.

Ma, Ya-Jun, et al., “Targeted magnetic resonance imaging (tMRI) of small changes in the T1 and spatial properties of normal or near normal appearing white and gray matter in disease of the brain using divided subtracted inversion recovery (dSIR) and divided reverse subtracted”, Quantitative Imaging in Medicine and Surgery.

* cited by examiner

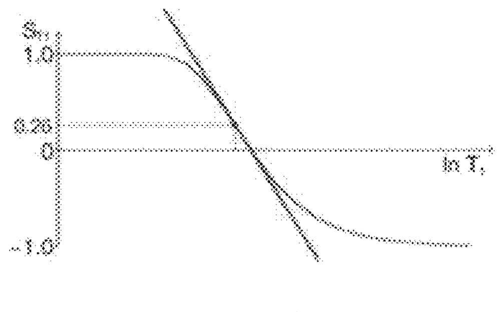
FIG. 7A
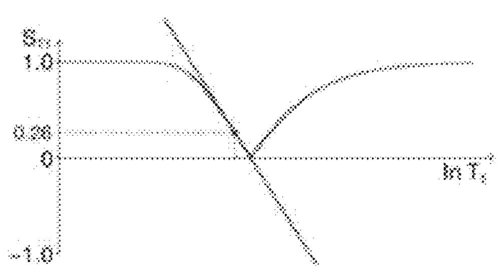
FIG. 7B
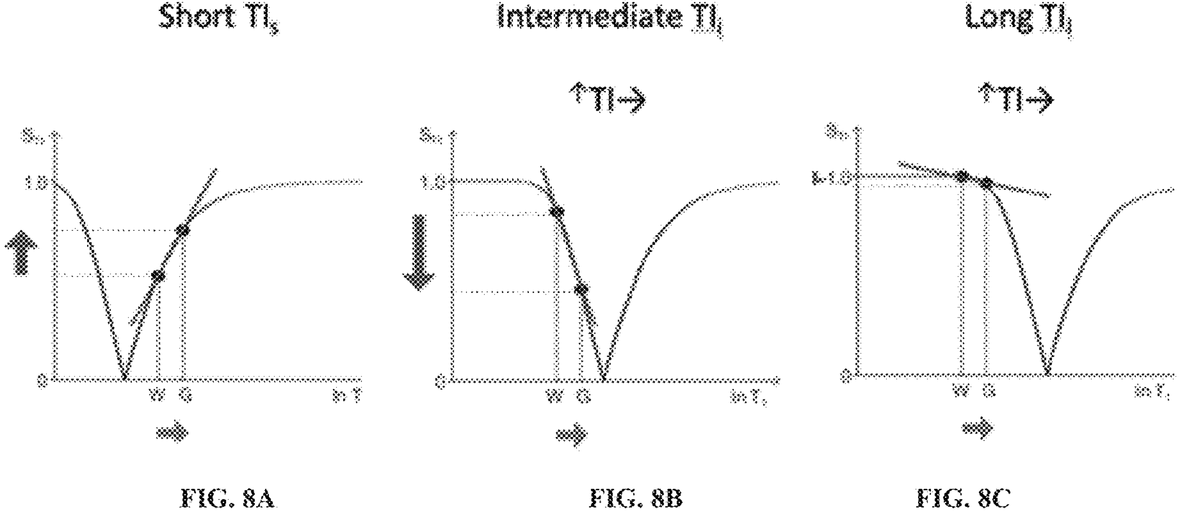
FIG. 8A
FIG. 8B
FIG. 8C

With linear X axis, i.e. TP $$C_{fr} = \sum_{TP}^{n} \frac{1}{S_{TP}} \frac{\partial S_{TP}}{\partial TP} \cdot \Delta TP$$

With logarithmic X axis, i.e. lnTP $$C_{fr} = \sum_{TP}^{n} \frac{1}{S_{TP}} \frac{\partial S_{TP}}{\partial \ln TP} \cdot \frac{\Delta TP}{TP}$$

$C_{fr}$ = ΔS/S, fractional contrast

TP = $\rho_m$, $T_1$, $T_2$, $T_2^*$, $D^*$, $T_2/T_1$ .....

$S_{TP}$ = TP-filter for each pulse sequence SE, IR, PGSE, SGE, bSSFP ..

$\frac{\partial S_{TP}}{\partial TP}$ = first partial derivative of $S_{TP}$ with respect to TP for linear X axis; is sequence weighting and slope of filter $\frac{\partial S_{TP}}{\partial \ln TP}$ = first partial derivative of $S_{TP}$ with respect to lnTP for logarithmic X axis; is sequence weighting and slope of filter $\Delta TP$ = difference or change in TP $\frac{\Delta TP}{TP}$ = fractional difference or change in TP

FIG. 11

Division of
subtraction
1.0
0.5
-0.5
-1.0
500
1000
1500
2000
2500
3000

Subtraction
1.0
0.8
0.6
0.4
0.2
-0.2
-0.4
0

Division of
subtraction

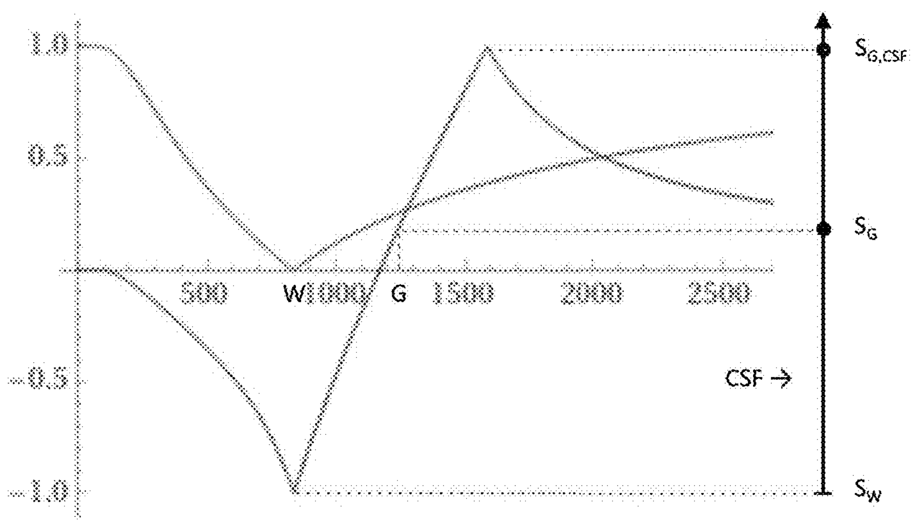
FIG. 24
FIG. 25

Methamphetamine addiction patient
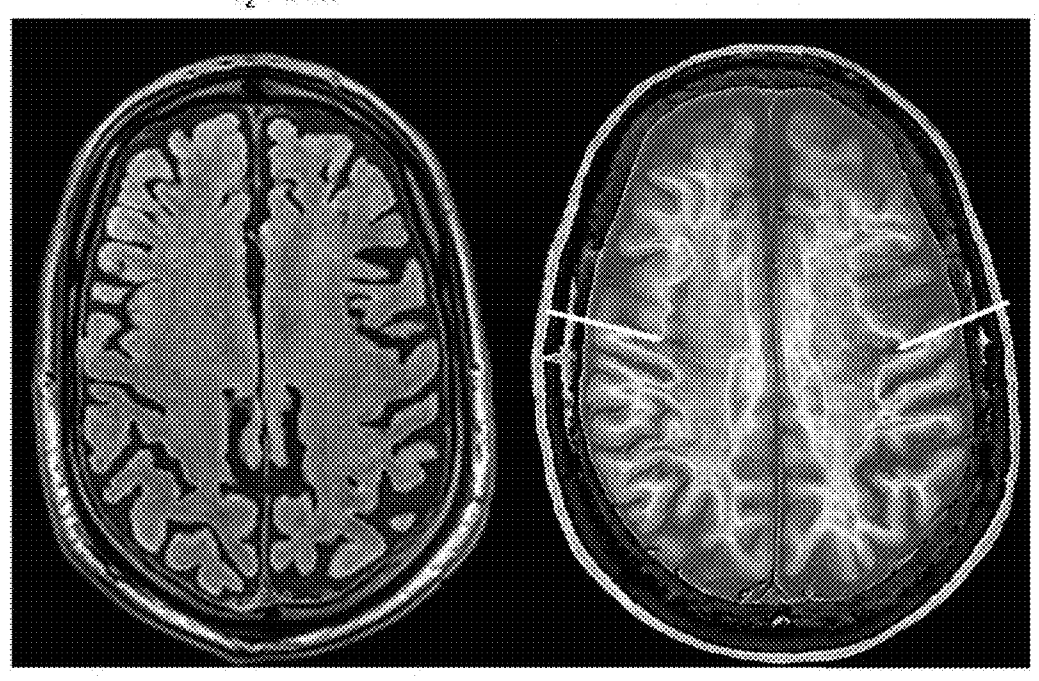
FIG. 35A
FIG. 35B

MRI CONTRAST USING SYNTHETIC PULSE SEQUENCES

CLAIM OF PRIORITY

This patent application claims the benefit of priority of U.S. Provisional Patent Application Ser. No. 63/585,740, filed on Sep. 27, 2023, which is hereby incorporated by reference herein in its entirety.

TECHNICAL FIELD

This document pertains generally, but not by way of limitation, to magnetic resonance in which a sequence is tailored to provide image contrast.

BACKGROUND

Magnetic resonance imaging (MRI) uses a magnetic field and radio frequency (RF) signals to generate data from which an MR image can be produced. For example, following excitation using an RF input signal, magnetic spins exhibit particular behavior that can be presented as an MR image. Images can be useful for identifying various tissue properties and/or disease states.

Under certain conditions, the contrast between healthy tissue and diseased tissue can be difficult to discern.

SUMMARY

An example of the present subject matter includes directly acquired and synthetic forms of imaging sequences using bipolar filters (BLAIRs) which provide increased image contrast that can reveal disease or conditions that are not seen on conventional images.

An example of the present subject matter includes synthesis of divided subtracted inversion recovery, and divided reverse subtracted inversion recovery images. These are examples of multiplied added subtracted and/or divided inversion recovery (MASDIR) images.

An example of the present subject matter includes synthesis of multiplied added subtracted and/or divided echo acquisition (MASDEA) images.

One example allows synthesis of narrower middle Domain (mD) dSIR and drSIR images from wider mD dSIR and drSIR images using a $T_1$-bipolar filter. This can provide a series of progressively smaller magnitude ΔTI images to improve contrast for different $\Delta T_1$s within the mD of the wider dSIR or drSIR image.

One example enables creation of synthetic dSIR and drSIR images from $T_1$ maps produced from sources such as MP2RAGE, shMOLLI, actual flip angle-ultrashort TE (UTE), MR fingerprinting and other techniques, using $T_1$-bipolar filters. The synthetic images provide flexibility for targeting different $T_1$s and generating contrast using different TIs without requiring direct acquisition of data for images.

One example includes synthetic $T_2$-, $T_2$*- and D*-bipolar filter images using $T_2$, $T_2$* and D* maps.

One example includes multiplication of $T_1$-, $T_2$-, $T_2$*- and/or D*-bipolar filter images to create synergistic contrast.

Each of these non-limiting examples can stand on its own, or can be combined in various permutations or combinations with one or more of the other examples of synthetic images.

This is intended to provide an overview of subject matter pertinent to the present patent application. It is not intended to provide an exclusive or exhaustive explanation of the invention. The detailed description is included to provide further information about the present patent application.

BRIEF DESCRIPTION OF THE DRAWINGS

FIGS. 7A and 7B illustrate inversion recovery $T_1$-filters with phase-sensitive (ps) (FIG. 7A) and magnitude (m) reconstruction (FIG. 7B) using ln $T_1$ axes, according to one example.

FIGS. 8A, 8B, and 8C illustrate long TR IR sequence with m reconstruction, according to one example.

FIG. 11 illustrates the central contrast theorem for MRI and a corollary, according to one example.

FIG. 24 shows use of a wide mD $T_1$-bipolar filter in which maximum signal is reached with a $T_1$ between those of gray matter and CSF, according to one example.

FIG. 25 illustrates partial volume effects between gray matter and CSF, according to one example.

FIGS. 35A and 35B compare a $T_2$-FLAIR image with a narrow mD dSIR image, according to one example.

DETAILED DESCRIPTION

1. Overview of Aspects

Figure 1:
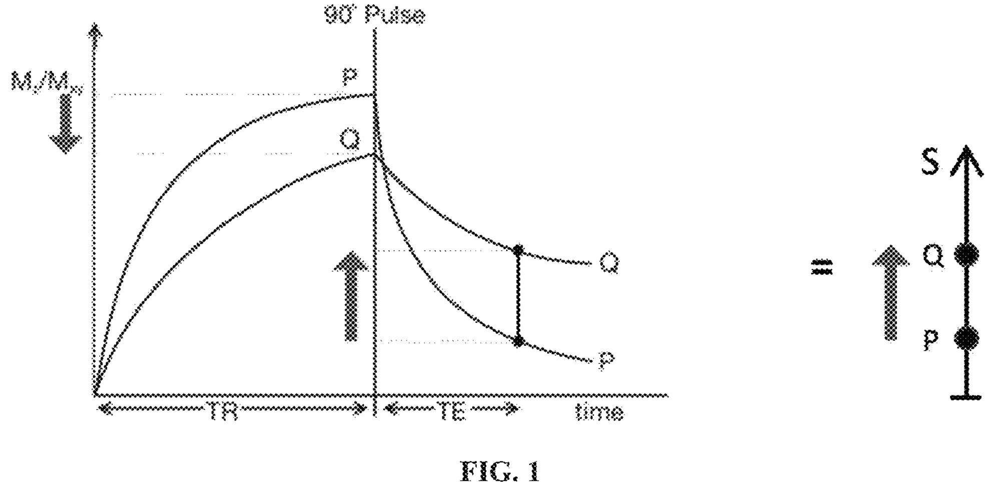
FIG. 1 illustrates a plot of $M_Z/M_{XY}$ vs time for the SE sequence for two example tissues.

An example of the present subject matter provides increased contrast in MRI using synthetic MASDIR and MASDEA images as well as synthetic $T_1$-, $T_2$-, $T_2$*- and/or D*-bipolar filter images using $T_1$, $T_2$, $T_2$* and/or D* maps.

Examples of the present subject matter can be understood by modelling using the modified Bloch equations and the concepts of Tissue Property filters (TP-filters) and the Central Contrast Theorem (CCT), as well as by other calculations.

A number of aspects are described as follows:

Aspect 1: Tissue Property-Filters (TP-Filters)

This includes a reformulation of the Bloch equations in which the variable time used in the equations takes constant values such as repetition time (TR), echo time (TE) and inversion time (TI), and treats the time constants $T_1$ and $T_2$ as variables.

Output is a series of plots of signal against tissue properties (TPs) such as mobile proton density ($\square_m$), $T_1$, $T_2$ and D*, chemical shift and susceptibility ($\square$) which are described as TP-filters.

This arrangement provides an improved description of the signal, contrast and weighting of pulse sequences rather than using the Bloch equations in standard form which plots signal against time.

For example, $T_1$-, $T_2$-, $T_2$*- and/or D*-bipolar filters are particularly helpful in understanding and using synthetic $T_1$, $T_2$, $T_2$* and/or D* images of the type described herein.

Aspect 2: The Central Contrast Theorem (CCT)

The Central Contrast Theorem can be derived from the Bloch equations. It has two components:

(i) With TP-filters, change in a TP in disease, or for other reasons, is plotted along the X axis and this is multiplied by the slope of the TP-filter to give the change in signal or contrast produced by the TP-filter. This is shown along the Y axis.

(ii) The total contrast produced by different TPs used in a sequence is the algebraic sum of the contrasts produced by each TP-filter.

The Central Contrast Theorem can be characterized by components (i) and (ii). The CCT identifies the sign and size of contrasts produced by changes in different TPs and reveals contributions to the overall contrast seen on MR images. It shows explicitly why the increased slope of the $T_1$-bipolar filter makes disease due to small changes in $T_1$ visible with directly acquired and synthetic dSIR and drSIR sequences when the disease is not seen with conventional sequences.

Aspect 3: Multiplied Added Subtracted and/or Divided Inversion Recovery (MASDIR) Pulse Sequences A combination of two or more inversion recovery (IR) sequences can be multiplied, added, subtracted and/or divided one or more times in a single sequence. The combinations of IR sequences can increase the contrast or specificity of MR imaging. The term MASDIR can be used to describe this group of sequences.

Aspect 4: Multiplied Added Subtracted and/or Divided Echo Acquisition (MASDEA) Sequences A combination of two or more echo acquisitions e.g. Ultrashort TE/Zero Echo TE (UTE/ZTE), Gradient Echo (GE), Spin Echo (SE) Pulsed Gradient Spin Echo (PGSE) and/or fat and/or water selective sequences using multiplication, addition, subtraction or division. For example, a divided MASDEA sequence can increase signal from ultrashort $T_2$ tissue components. Examples are shown in Table 3. The term MASDEA can be used to describe this group of sequences.

Aspect 5: Synergistic Contrast MRI (scMRI)

One example considers a single TP such as $T_1$ used twice or more in a single pulse sequence to increase net, or overall contrast. One example considers two or more different TPs such as $T_1$ and $T_2$ used in the same sequence to increase the net contrast produced by both of them. Synergistic contrast MRI may use change in $T_1$ up to 3 or 4 times in the same sequence to increase contrast as with directly acquired and synthetic dSIR and drSIR sequences. The term scMRI can be used to refer to synergistic contrast MRI where multiple contributions from the same or different TPs contribute to produce increased contrast. Synergistic contrast can be seen on both directly acquired and synthetic images.

Aspect 6: Targeted Magnetic Resonance Imaging (tMRI)

A pulse sequence can be tailored to specifically target, for example, a single tissue (e.g. white or gray matter), as well as change in a single TP of that tissue such as $T_1$ including the sign and size of the change in the TP in disease. The term tMRI can refer to a single TP or several TPs. A tMRI sequence is a pulse sequence targeted specifically at a single tissue or change in a TP of that tissue in disease or due to contrast agents. For example, tMRI can be used for imaging subtle increases in $T_1$ in normal appearing white or gray matter due to disease of the brain using directly acquired and synthetic narrow middle Domain (mD) dSIR and drSIR sequences.

Aspect 7: Contrast at Boundaries

Contrast at tissue boundaries in an image includes voxels having mixtures of different tissues (i.e. there are partial volume effects). A derivative, namely change in signal (or contrast) with distance x, is used to describe tissue boundaries on images. In this situation, the contributions to this derivative are from sequence weighting, change in tissue fraction (f, the proportion of a tissue in the voxel) with TP, and change in f with distance x. This formulation provides an understanding of contrast at boundaries. For example, partial volume effects can produce high signal white lines seen at the boundaries between white and gray matter on directly acquired and synthetic narrow mD dSIR and drSIR images.

Aspect 8: Small Change Regimes

Small changes relative to normal TPs (such as $T_1$) can indicate diseased tissue. These allow the use of small change approximation in calculus. In addition, rigid body registration can be used to align isotropic synthetic 3D (three Dimensional) MASDIR and other images to detect small changes between images in serial MRI studies performed at different times. The small change approach can be applied to high signal boundaries such as those seen with MASDIR and other directly acquired and synthetic images.

Aspect 9: Tissue Property Mapping

Divided subtracted inversion recovery (dSIR) and divided reverse subtracted inversion recovery (drSIR) images are $T_1$ maps in the middle Domain (mD). Divided subtracted inversion recovery (dSIR) and divided reverse subtracted inversion recovery (drSIR) images can give direct readings of $T_1$ for tissues shown in the mD without requiring an additional $T_1$ mapping sequence. Synthetic $T_1$-, $T_2$-, $T_2$*- and D*-bipolar filter images also provide TP maps in the mD.

Aspect 10: Synthetic MASDIR and MASDEA Bipolar Filter (BLAIR) Images (a) Wider mD dSIR and drSIR images can be used to create synthetic narrower mD dSIR and drSIR ($T_1$-bipolar filter) images. (b) $T_1$ maps can be used to create synthetic $T_1$-bipolar filter dSIR and drSIR images. (c) $T_2$, $T_2$* and D* maps can be used to produce synthetic $T_2$-, $T_2$*- and D*-bipolar filter images as well. (d) Synthetic TP-bipolar filter images can be combined to produce increased synergistic contrast using different TPs such as $T_1$, $T_2$, $T_2$* and D*.

Aspect 11: Imaging of Normal Appearing Tissues

Directly acquired divided subtracted inversion recovery (dSIR) and divided reverse subtracted inversion recovery (drSIR, or combinations of these) images as well as synthetic $T_1$-, $T_2$-, $T_2$*- and D*-bipolar filter images can be configured to target small changes in $T_1$, $T_2$, $T_2$* and D* in normal appearing tissues where the small changes in TPs are insufficient to produce useful contrast with conventional pulse sequences. Thus, synthetic dSIR or drSIR and other TP-bipolar filter images can reveal abnormalities in normal appearing tissues such as white and gray matter of the brain when these are not apparent otherwise.

Aspect 12: Ultra-High Contrast MRI (UHC MRI)

Synthetic TP-bipolar filter images can produce an order of magnitude increase in contrast or more compared with conventional inversion recovery and other sequences. This allows previously imperceptible changes in $T_1$, $T_2$, $T_2$* and D* to be manifest as changes in contrast with these sequences.

A similar order of magnitude increase in contrast can be produced by changing opposed $T_1$ and $T_2$ contrast, as well as by changing opposed $T_2$ and diffusion contrast. The changes are made to make contrast synergistic for $T_1$ and $T_2$ as well as $T_2$ and diffusion contrast respectively. This is done using synthetic MASDIR, MASDEA and $T_1$-, $T_2$-, $T_2$*- and D*-bipolar filter images.

In some examples, white matter can appear normal using conventional sequences but show extensive abnormalities when imaged with a TP-bipolar filter sequence. This can be helpful for identifying disease and for ruling out the presence of occult disease with greater certainty. In one example, this entails using an additional TP-bipolar filter sequence that is more sensitive to small changes in TPs than conventional sequences and can therefore exclude more subtle disease.

Benefits achieved can include creation of precise boundaries between white and gray matter in the brain, direct measurement of TPs, increased sensitivity to Gadolinium Based Contrast Agent (GBCA) enhancement, observation of changes in serial studies, and quantification. The quantification includes changes in $T_1$ in disease and after GBCA administration, as well as changes in the spatial properties (site, size, surface, etc) of normal structures and tissues in serial studies.

According to one example, synthetic imaging allows creation of TP-bipolar filter images with different contrasts due to the TPs $T_1$, $T_2$, $T_2$* and D* from a single acquisition which maps these TPs.

The disclosed subject matter can be used for imaging the nervous system, the body, the musculoskeletal system and the cardio-respiratory system in adults as well as children.

2. Additional (Items 2.01-2.13)

2.01 Tissue Property Filters (TP-Filters)

2.01.1 the Spin Echo (SE) Sequence

Image signal and contrast seen with the SE sequence can be described using the Bloch equations. Firstly, it follows longitudinal magnetization ($M_Z$) over time TR, and secondly, it follows transverse magnetization ($M_{XY}$) after the application of a 900 pulse (FIG. 1) for further time TE. Contrast between two example tissues, such as tissue P with a shorter $T_1$ and $T_2$, and tissue Q with a longer $T_1$ and $T_2$, is shown by the difference in $M_{XY}$ at the time of data collection (dc) at TE as shown in FIG. 1.

FIG. 1 illustrates a plot of $M_Z/M_{XY}$ vs time for the SE sequence for tissue P (with a shorter $T_1$ and $T_2$) and tissue Q (with a longer $T_1$ and $T_2$). $T_1$-dependent contrast (first negative blue arrow on left), and overall $T_1$ and $T_2$ contrast (second=third positive blue arrows in center and on right) are shown.

The voxel signal S for a SE sequence is derived from the simplified Bloch equations so that:

$$S = K\square_m\left(1 - e^{-t'/T1}\right)e^{-t''/T2} \qquad [1]$$

where K is a scaling function, $\square_m$ is the mobile proton density, t' is time for the second segment and t" is time for the third segment of equation [1]. $T_1$ and $T_2$ are time constants. Eq. [1] describes $\square_m$ in the first segment, recovery of longitudinal magnetization ($M_Z$) over time in the second segment (which is in parentheses), and decay of transverse magnetization ($M_{XY}$) over time in the third segment. The equations in the second and third segments are of the forms $y=1-e^x$ and $y=e^x$ respectively.

Eq. [1] describes the signal of a tissue (with specific values of $T_1$ and $T_2$) for a SE pulse sequence for specific values of TR and TE. To compare different tissues, at least two curves are plotted as in FIG. 1.

It is useful to replace the variables t' and t" in Eq. [1] by the constant times of the SE sequence TR and TE, and to treat the two time constants $T_1$ and $T_2$ in Eq. [1] as variables. This changes Eq. [1] to:

$$S = K\square_m\left(1 - e^{-TR/T1}\right)e^{-TE/T2} \quad [2]$$

or:

$$S = KS\square_m S_{T1} S_{T2} \quad [3]$$

where the signals for the three segments $S\square_m$, $S_{T1}$ and $S_{T2}$ are given by:

$$S\square_m = \square_m,\ S_{T1} = 1 - e^{-TR/T1},\ S_{T2} = e^{-TE/T2} \quad [4]$$

The second and third segments in Eq. [2] are of the forms $y=1-e^{-i/x}$ and $y=e^{-1/x}$ respectively (since $T_1$ and $T_2$ are now variables). These forms are quite different from the forms $y=1-e^{-x}$ and $y=e^{-x}$ shown in the second and third segments of the Bloch equations in Eq. [1].

Figure 2A:
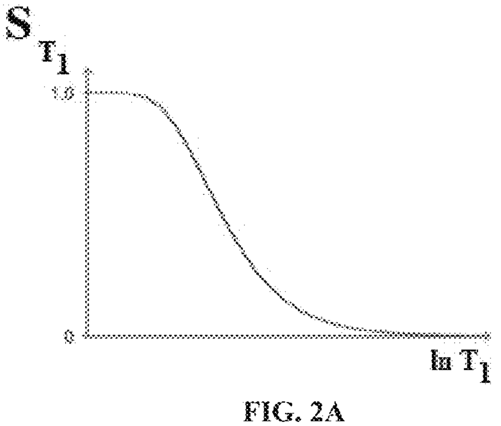
FIGS. 2A and 2B illustrate spin echoes T1 and T2, respectively, according to one example.
Figure 2B:
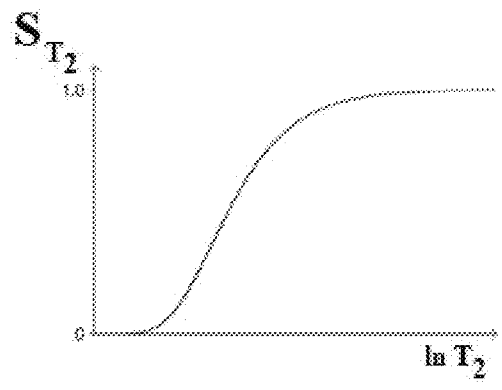

The three segments of Eqs. [2]-[4] have the features of a linear or exponential filter for $^{-}{}_m$, (depending on whether the X axis is linear or natural logarithmic (ln)), a low pass filter for $T_1$ (FIG. 2A) and a high pass filter for $T_2$ (FIG. 2B).

FIGS. 2A and 2B illustrate spin echoes T1 and T2, respectively. In FIG. 2A, the plot shows $S_{T1}$ vs ln $T_1$. In FIG. 2B, the plot shows $S_{T2}$ vs ln $T_2$. The $T_1$-filter (FIG. 2A) has the appearance of a low pass filter and the $T_2$-filter (FIG. 2B) has that of a high pass filter. Low values of $T_1$ "pass" in (FIG. 2A) and high values of $T_2$ "pass" in (FIG. 2B).

The signal levels on images are given by Eqs. [2]-[4] for S $^{-}{}_m$, $S_{T1}$ and $S_{T2}$, and correspond to the signal or brightness of tissues seen on images.

Eqs. [2]-[4] can be plotted using a linear or a logarithmic X axis. When using a linear axis, changes in x (i.e. changes in $_{-m}$, $T_1$ or $T_2$) represent absolute differences in TPs. When using a logarithmic X axis, small changes in x (i.e. □ ln$\sqcup_m$, $\sqcup$ln$T_1$ and $\sqcup$ln$T_2$) are fractional changes in TPs because for small differences in x, □ln x=□x/x.

Figure 3:
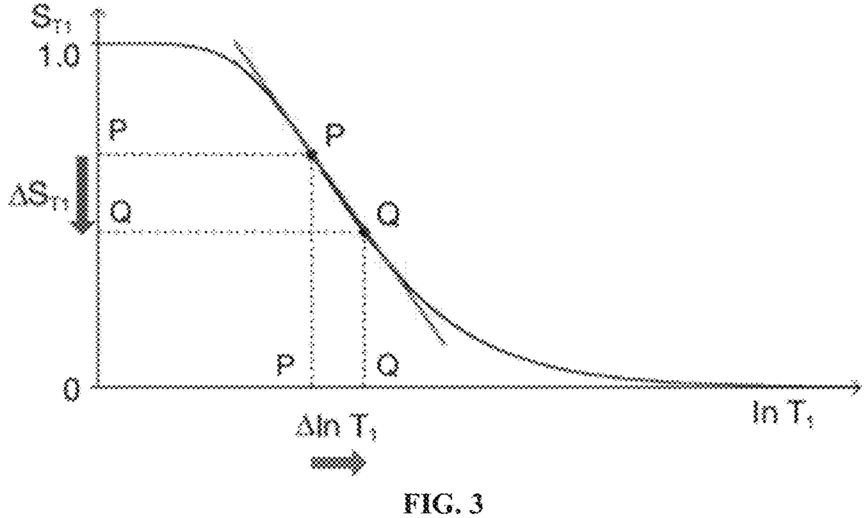
FIG. 3 shows a spin echo sequence, according to one example.

Absolute contrast ($C_{ab}$) or difference in signal □$S_{T1}$ produced by a difference $$\square \ln T_1 \left(= \frac{\Delta T_1}{T_1}\right)$$

between the $T_1$s of two tissues P and Q is shown in FIG. 3 using a ln X axis.

FIG. 3 illustrates an SE sequence. $T_1$-filter with a ln $T_1$ X axis. The positive increase in $T_1$ from P to Q □ln $T_1$ (horizontal green arrow) is multiplied by the negative slope of the $T_1$-filter (red line) to give negative contrast (vertical blue arrow) □$S_{T1}$=$C_{ab}$. □$S_{T1}$ may be positive or negative. _ ln $T_1$ may also be positive or negative.

A positive change from P to Q of $\sqcup$ln$T_1$ along the X axis produces a negative change from P to Q along the Y axis, or negative change in signal $\sqcup S_{T1}$ i.e. contrast $C_{ab}$=$\sqcup S_{T1}$.

The equation for $C_{ab}$ for small changes in □ $_{T1}$ and □ $S_{T1}$ using a linear X axis is:

$$C_{ab} = \Delta S_{T_1} = \frac{\partial S_{T_1}}{\partial T_1} \cdot \Delta T_1 \quad [5]$$

where $$\frac{\partial S_{T_1}}{\partial T_1}$$

is the first partial derivative of the $T_1$-filter with respect to $T_1$, or the slope of the $T_1$-filter, ·=multiplied, and □ $T_1$ is the change in $T_1$ using a linear X axis.

Using a in X axis, and noting that $$\square \ln T_1 = \frac{\Delta T_1}{T_1}$$

for small changes in $T_1$, and that $$\frac{dy}{d(\ln x)} = x\frac{dy}{dx},$$

where x is a variable, Eq. [5] becomes:

$$C_{ab} = \Delta S_{T_1} = \frac{\partial S_{T_1}}{\partial \ln T_1} \cdot \frac{\Delta T_1}{T_1} \quad [6]$$

where $$\frac{\partial S_{T_1}}{\partial \ln T_1}$$

is the slope of the filter, or the first partial derivative with respect to ln$T_1$ (when using a in X axis), ·=multiplied, and $$\frac{\Delta T_1}{T_1}$$

is the fractional change in $T_1$ as in FIG. 3. For the $T_1$-filter, positive change from P to Q along the X axis results in negative change from P to Q along the Y axis i.e. negative contrast $C_{ab}$. The slope of the curve, which is the sequence weighting for the TI segment, is negative.

For the $T_2$-filter (FIG. 4), positive change $$\square \ln T_2 = \frac{\Delta T_2}{T_2}$$

from P to Q along the X axis results in positive change □ $S_{T2}$=$C_{ab}$ from P to Q along the Y axis i.e. positive contrast. The slope of the $T_2$-filter, which is the sequence weighting for the $T_2$ segment, is positive.

Figure 4:
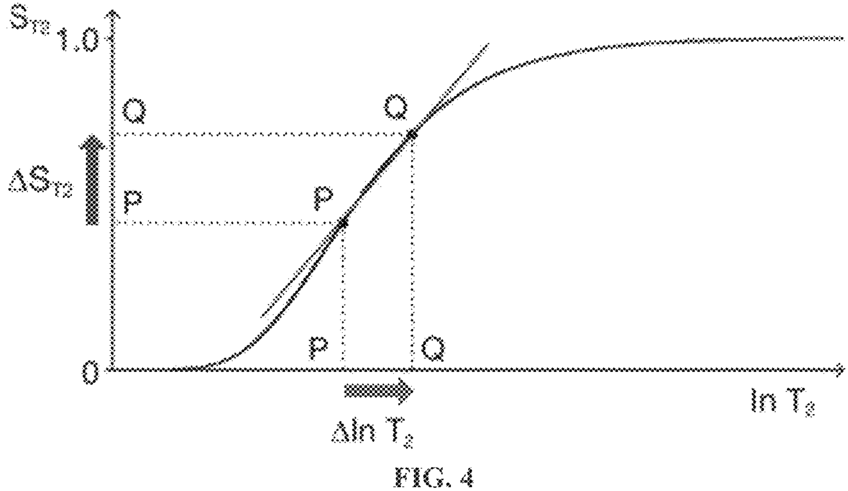
FIG. 4 illustrates a spin echo sequence, according to one example.

FIG. 4 illustrates a spin echo sequence. $T_2$-filter with ln $T_2$ X axis. The positive increase in $T_2$ from P to Q □ ln $T_2$ (horizontal green arrow) is multiplied by the positive slope of the $T_2$-filter (red line) to give positive contrast (vertical blue arrow) □ $S_{T2}$=$C_{ab}$.

Solving for the situation when the second derivative of the TP-filter is equal to zero yields the TIP value where the slope of the TP-filter, and therefore the contrast, is highest. For the $T_1$- and $T_2$-filters, the slope is greatest at TR=$T_1$ and TE=$T_2$ when using a ln X axis, and at TR=2$T_1$ and TE=2$T_2$ when using a linear X axis.

Figure 5:
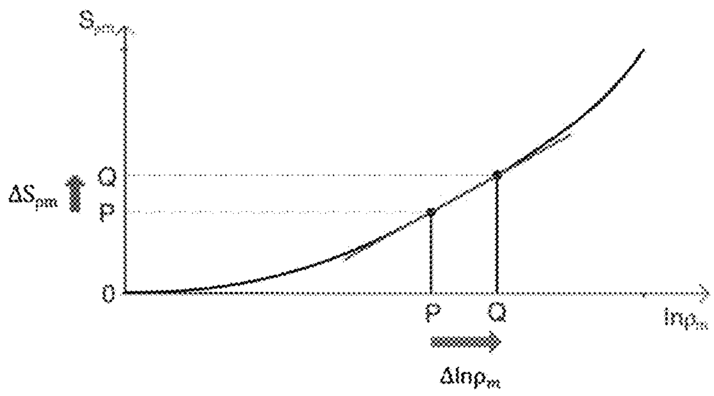
FIG. 5 illustrates an example of a spin echo sequence.

A similar pattern for contrast applies to □$_m$ where an increase in □ln □$_m$ and positive slope of the □$_m$-filter produce positive contrast □S□$_m$=$C_{ab}$ (FIG. 5).

FIG. 5 illustrates an example of a spin echo sequence. SE sequence. □$_m$-filter with ln $Q_m$ X axis. The positive increase in □$_m$ from P to □ln □$_m$ (horizontal green arrow) is multiplied by the positive slope of the □$_m$-filter (red line) to give positive contrast (vertical blue arrow) □S□$_m$=$C_{ab}$.

For fractional contrast $C_{fr}$=□S/S (rather than $C_{ab}$=□S), Eqs. [5] and [6] are divided by $S_{T1}$ and $S_{T2}$ respectively for non-zero values of $S_{T1}$ and $S_{T2}$.

So, for $T_1$ using a ln X axis:

$$C_{fr} = \frac{1}{S_{T_1}} \frac{\partial S_{T_1}}{\partial \ln T_1} \cdot \frac{\Delta T_1}{T_1} \quad [7]$$

and for $T_2$ using a ln X axis:

$$C_{fr} = \frac{1}{S_{T_2}} \frac{\partial S_{T_2}}{\partial \ln T_2} \cdot \frac{\Delta T_2}{T_2} \quad [8]$$

The TP-filters can be considered separately (i.e. a univariate model for each TP alone, as above), or be combined in a mulvariate model. This shows the contributions of the sequence weightings and changes in each TPs to overall contras (for each of □$_m$, $T_1$ and $T_2$ in the SE sequence and is illustrated in FIG. 6.

Figure 6:
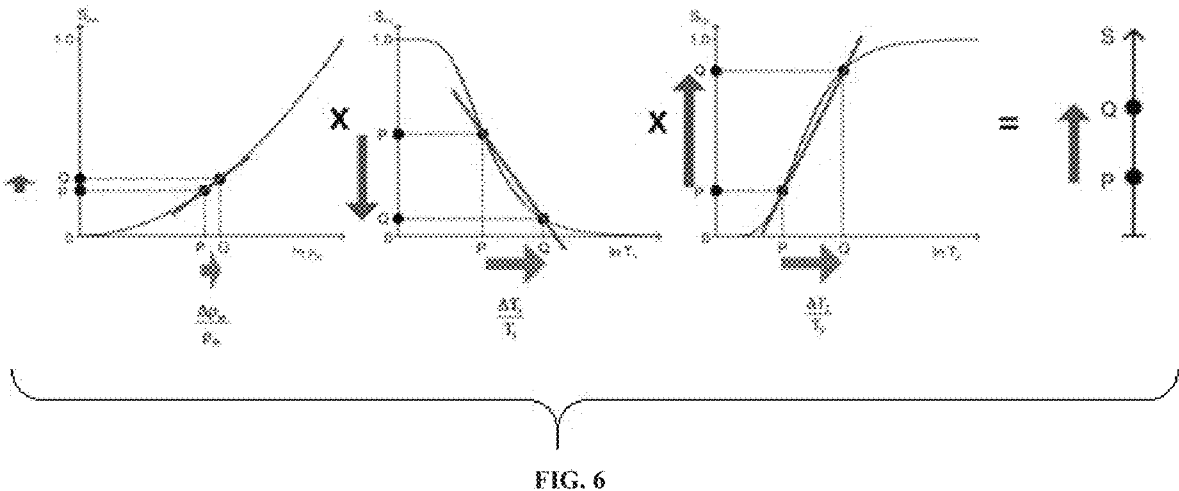
FIG. 6 illustrates a spin echo sequence with combination of $\square_m$-, $T_1$- and $T_2$-filters, according to one example.

FIG. 6 illustrates a spin echo sequence with combination of □$_m$-, $T_1$- and $T_2$-filters. Increases in □□$_m$/□$_m$, □$T_1/T_1$ and □$T_2/T_2$ (horizontal green arrows) are multiplied by the slopes of their respective TP-filters (red lines) to produce positive, negative, and positive □$_m$, $T_1$ and $T_2$ contrasts from their filters (vertical blue arrows with each filter). The overall contrast (blue arrow on right) is the algebraic sum of the TP contrasts produced by each of the three filters (blue arrows with each filter).

2.01.2. The Inversion Recovery (IR) Sequence

The IR sequence has an additional $T_1$-filter (segment) to those of the SE sequence shown in FIGS. 7A and 7B for which:

$$S_{T1} = \left(1 - 2e^{-TI/T1}\right) \quad [9]$$

This $T_1$-filter is shown in phase-sensitive (ps) reconstructed form in FIG. 7A and in magnitude (m) reconstructed form in FIG. 7B.

FIGS. 7A and 7B illustrate inversion recovery $T_1$-filters with phase-sensitive (ps) (FIG. 7A) and magnitude (m) reconstruction (FIG. 7B) using ln $T_1$ axes. FIG. 7A shows both positive and negative values for $S_{T1}$ whereas in FIG. 7B, negative values are "reflected" across the X axis and become positive. The maximum slopes of the $T_1$-filters are shown as red lines and are negative in both cases.

When TI is increased, the $T_1$-filter shifts to the right as shown for the long repetition time (TR) m form of the IR sequence in FIGS. 8A, 8B, and 8C.

FIGS. 8A, 8B, and 8C illustrate long TR IR sequence with m reconstruction. $T_1$-filters for short TIs (shown in FIG. 8A), intermediate $TI_1$ (shown in FIG. 8B) and long $TI_1$ (shown in FIG. 8C) values. The positions of white (W) and gray (G) matter are the same for each TI. TI is increased from $TI_s$ (FIG. 8A) to $TI_i$ (FIG. 8B) and then further to $TI_1$ (FIG. 8C). The increase in $T_1$ from W to G (green arrows) is multiplied by the relevant slopes of the $T_1$-filters (red lines) and produces strongly positive, strongly negative, and mildly negative contrast respectively, as TI is increased from left to right (blue arrows).

FIG. 8A shows the IR $T_1$-filter with a short TIs (e.g. the STIR sequence) for the brain where gray matter (G) has a higher signal than white matter (W). The slope of the $T_1$-filter between W and G is strongly positive. When TI is increased to an intermediate $TI_i$ as in FIG. 8B with W and G fixed in the same position on the ln X axis, W now has a higher signal than G. The slope of the $T_1$-filter between them is strongly negative. When $TI_i$ is increased further to a long $TI_i$ as in FIG. 8C, W is slightly higher signal than G and the slope of the $T_1$-filter between them is negative but of smaller size than in FIG. 8B. The sequence weighting, which is the slope or first partial derivative of the $T_1$-filter is highly positive in (FIG. 8A), highly negative in (FIG. 8B) and slightly negative in (FIG. 8C) using a short TIs (FIG. 8A), an intermediate $TI_i$ (FIG. 8B) and a long $TI_i$(FIG. 8C) respectively. When TR>>$T_1$ with the IR sequence the other $T_1$-filter ($1-e^{-TR/T1}$) becomes −1 and the main determinant of contrast is the ($1-2e^{-TI/T1}$) $T_1$-filter.

2.01.3 the Pulsed Gradient Spin Echo (PGSE) Sequence

Figure 9:
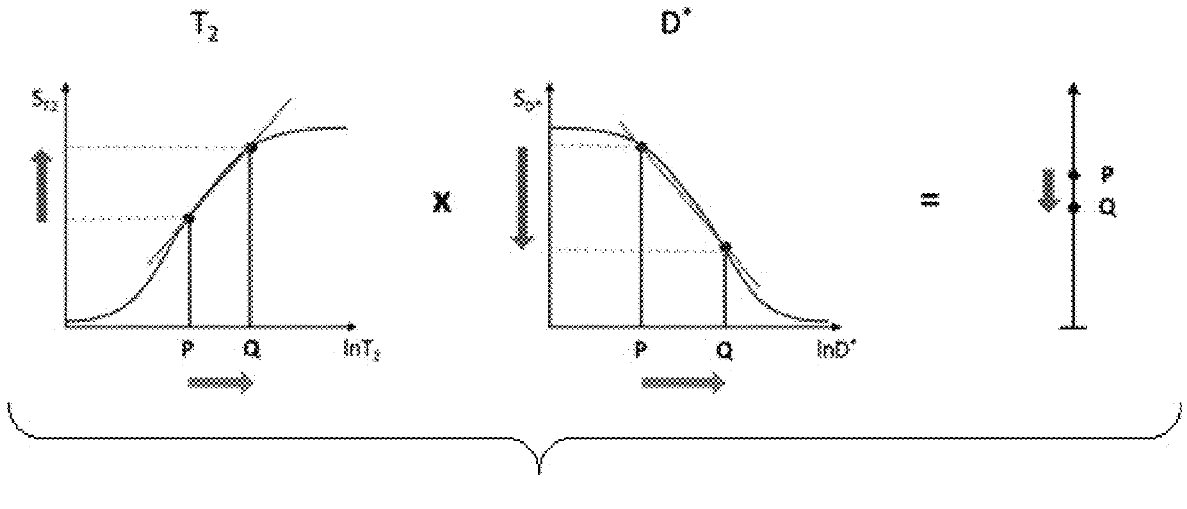
FIG. 9 illustrates PGSE sequence $T_2$- and D*-filters, according to one example.

For diffusion using the PGSE sequence an additional segment is added to those shown in FIG. 6 for the SE sequence and is illustrated in FIG. 9 under the heading D*.

FIG. 9 illustrates PGSE sequence $T_2$- and D*-filters. Increases in both $T_2$ and D*from P to Q (positive horizontal green arrows) result in positive and negative contrast respectively, and low opposed negative overall contrast (blue arrow, right).

The extra segment is the D*-filter and has the form of an exponential decay with its signal $S_D{}^*=e^{-bD*}$ where b is the diffusion sensitivity parameter and D* is the apparent diffusion coefficient. Significant D*-weighting requires a long TE with the PGSE sequence using present day clinical scanners. This is to provide time for the two pulsed diffusion gradients to be applied before and after the inversion pulse of the SE sequence. The long TE necessary for this creates $T_2$-weighting and so the sequence simultaneously has positive $T_2$-weighting (positive slope of the $T_2$-filter shown in FIG. 9 under the heading $T_2$), and negative D*-weighting (negative slope of the D*-filter shown in FIG. 9 under the heading D*). Positive change D $T_2$ from P to Q along the X axis (horizontal green arrow, □$T_2$) produces positive $T_2$ contrast (positive vertical blue arrow). Positive change □D* from P to Q along the X axis (horizontal green arrows, □D*) produces negative D* contrast (negative vertical blue arrow). The result of the opposed $T_2$ and D* contrasts produced in this way is low overall negative contrast (negative vertical blue arrow on the right). This is the case in many tissues where disease produces an increase in both $T_2$ and D*, and the resulting opposed diffusion and $T_2$ contrasts produce low overall contrast.

Figure 10:
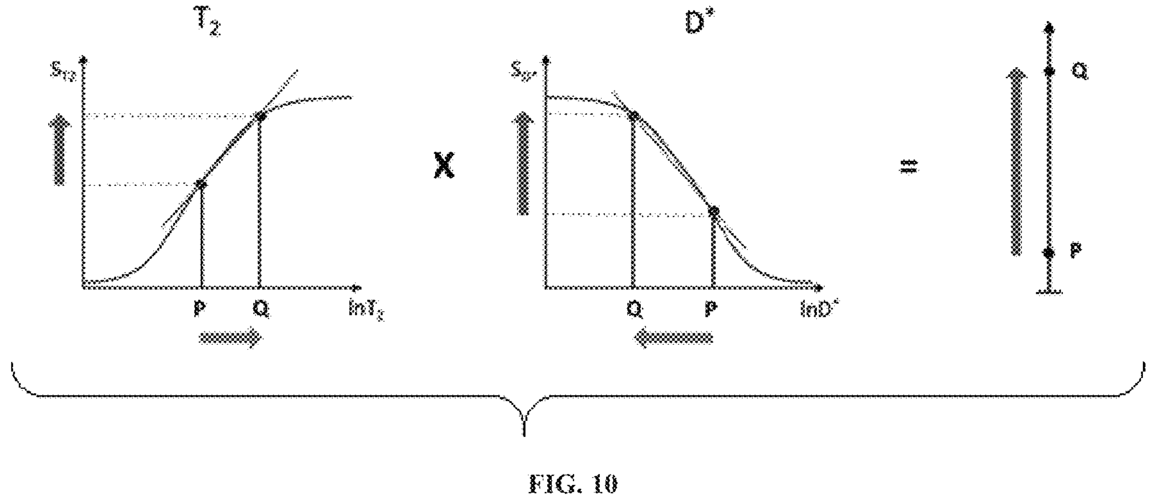
FIG. 10 illustrates PGSE sequence $T_2$- and D*-filters, according to one example.

FIG. 10 shows the situation when $T_2$ is increased from P to Q under the heading $T_2$, and D* is decreased from P to Q under the heading D* (rather than increased as in FIG. 9). The changes in $T_2$ and D* both result in positive contrast (blue arrows) and the algebraic sum of these is synergistic and results in high positive contrast (vertical blue arrow on right). Thus, the PGSE $T_2$ and diffusion weightings work together with the changes in $T_2$ and D* to produce synergistic contrast.

FIG. 10 illustrates PGSE sequence $T_2$- and D*-filters. Increase in $T_2$ and decrease in D*from P to Q (positive and negative horizontal green arrows) both produce positive contrast and, as a consequence, high positive overall synergistic contrast (vertical blue arrow, right).

2.02 The Central Contrast Theorem (CCT)

From Eqs. [3] and [4] for small change in □ □$_m$, □$T_1$ and □$T_2$, and using a ln X axis, the product rule from differential calculus gives:

$$\Delta S = \frac{\partial S_{\rho_m}}{\partial \ln\rho_m} S_{T_1} S_{T_2} \cdot \frac{\Delta\rho_m}{\rho_m} + S_{\rho_m} \frac{\partial S_{T_1}}{\partial \ln T_1} S_{T_2} \cdot \frac{\Delta T_1}{T_1} + S_{\rho_m} S_{T_1} \frac{\partial S_{T_2}}{\partial \ln T_2} \cdot \frac{\Delta T_2}{T_2} \quad [10]$$

Normalizing Eq. [10] by dividing it by S and using Eq. [3], for non-zero values of S, S□$_m$, $S_{T1}$ and $S_{T2}$, $C_{fr}$ s given by:

$$C_{fr} = \frac{\Delta S}{S} = \frac{1}{S_{\rho_m}} \frac{\partial S_{\rho_m}}{\partial \ln\rho_m} . \frac{\Delta\rho_m}{\rho_m} + \frac{1}{S_{T_1}} \frac{\partial T_1}{\partial \ln T_1} \cdot \frac{\Delta T_1}{T_1} + \frac{1}{S_{T_2}} \frac{\partial S_{T_2}}{\partial \ln T_2} \cdot \frac{\Delta T_2}{T_2} \quad [11]$$

Thus, the contributions of the TPs to the overall contrast $C_{fr}$ are for each TP its sequence weighting multiplied by the fractional change in the TP.

From Eq. [11] the overall fractional contrast $C_{fr}$ using a ln X axis is given by:

$$C_{fr} = \sum\nolimits_{TP} \frac{1}{S_{TP}} \frac{\partial S_{TP}}{\partial \ln TP} \cdot \frac{\Delta TP}{TP} \quad [12]$$

where $1/S_{TP}\ \partial S_{TP}/\partial \ln TP$ is the sequence weighting for the TP and □TP/TP is the fractional change in the TP. This is one form of the Central Contrast Theorem (CCT) for MRI and its corollaries as shown in FIG. 11.

FIG. 11 illustrates the Central Contrast Theorem (CCT) for MRI and a corollary. The signal equations for $C_{fr}$ are shown with a linear X axis (TP) (upper) and with a logarithmic X axis (In TP) (lower). The theorem relates fractional contrast $C_{fr}$ to differences/changes in TPs.

Using a ln X axis, the contrast for each TP is the normalized first partial derivative with respect to lnTP multiplied by the fractional change in TP. The total fractional contrast $C_{fr}$ is the algebraic sum of the contributions to contrast from each TP. For $T_1$ and $T_2$, if both fractional contrasts are positive, or if both are negative, a synergistic contribution to overall $C_{fr}$ results. If one TP contrast is negative and the other is positive a reduction in overall $C_{fr}$ results. Thus, to achieve synergistic contrast, contributions to contrast of the same sign are sought from each of the relevant TPs to make their effects complementary.

2.03 MASDIR (Multiplied Added Subtracted and/or Divided IR) Pulse Sequences

2.03.1 Development of MASDIR Sequences

Two IR sequences can be used to form a single sequence. The two IR sequences can include two successive inversion pulses to suppress signal from fluid then fat, and when applied in the brain and body, can be referred to as the Double IR (DIR) sequence.

The two IR sequences can be configured to suppress either white or gray matter signals as well as CSF. MP2RAGE (Magnetization Prepared 2 Rapid Acquisition Gradient Echo) sequence entails multiplying two IR images together and normalizes them by dividing by the sum of the squares of the two images (3).

Another configuration can be referred to as Fluid And White matter Suppression (FLAWS) (4, 5).

2.03.2 Groups of MASDIR Sequences

A classification of MASDIR sequences is shown in Table 1. They are grouped into: (a) Multiplied, (b) Added, (c) Subtracted, and (d) Divided categories. The MASDIR sequences are discussed below.

TABLE 1

| Groups of MASDIR sequences | Expansion of MASDIR sequence acronyms |
|---|---|
| MIR | Multiplied IR |
| DIR | Double IR ($mTI_l \times mTI_{s/i}$) |
| MP2RAGE | Magnetization Prepared 2 Rapid Acquisition Gradient Echo ($psTI_l \times psTI_i$) (also 18ormalized) |
| AIR | Added IR |
| AIR | Added IR ($mTI_{s/i/l} + mTI_{s/i/l}$) |
| $A^1$IR | Added IR ($psTI_{s/i/l} + mTI_{s/i/l}$) |
| $A^1$IRES | AIR Added IR Echo Subtraction |
| $S^1$AIR | Subtracted, Added IR |
| SIR | Subtracted IR |
| SIR, rSIR | Subtracted IR ($mTI_{s/i/l} - mTI_{s/i/l}$), reverse SIR |
| SIRES, rSIRES | Subtracted IR Echo Subtraction, reverse SIRES |
| SIREDS, rSIRDES | Subtracted IR Echo Diffusion Subtraction, reverse SIREDS |
| SIRGES, rSIRGES | Subtraction IR Gradient Echo Subtraction, reverse SIRGES |
| SIRDGES, rSIRDGES | Subtraction IR Diffusion and Gradient Echo Subtraction, reverse SIRDGES |
| $S^1$IR | Subtracted IR ($psTI_{s/i/l} - mTI_{s/i/l}$) |
| $S^2$IR | Subtracted SIR |
| dIR | divided IR |
| dSIR, drSIR | divided SIR, divided reverse SIR |
| dSIRES, drSIRES | divided SIRES, divided reverse SIRES |
| dSIREDS, drSIREDS | divided SIREDS, divided reverse SIREDS |
| dSIRGES, drSIRGES | divided SIRGES, divided reverse SIRGES |
| dSIRDGES, drSIRDGES | divided SIRDGES, divided reverse SIRDGES |

Table 1 illustrates selected MASDIR Sequences (a) Multiplied IR (MIR) sequences.

MIR sequences include DIR and MP2RAGE as noted above.

(b) Added IR (AIR and $A^1IR$) sequences.

One group of AIR sequences adds two magnitude reconstructed sequences with different Tis and is used with subtraction and division (see below). Another group of sequences ($A^1IR$) use a single TI with images reconstructed in ps and m forms. Addition of these two sequences shows shorter $T_1$ tissues and suppresses the signal from longer $T_1$ tissues and fluids. The $A^1IRES$ sequence supplements this by Echo Subtraction (ES, see later) and so adds a $T_2$-filter reducing the signal from longer $T_2$ tissues and fluids to provide a combined short $T_1$ short $T_2$-filter. The Subtracted AIR ($S^1AIR$) sequence subtracts a longer TI image from a shorter one to selectively show a specific range of short $T_1$ tissues.

(c) Subtracted IR (SIR) Sequences.

Seven subgroups of SIR sequences are included in Table 1. The first five use subtraction of a longer TI image from a shorter TI one (or vice versa as the reversed or r form). They start with the basic sequence (SIR), add $T_2$-weighting to it as the SIRES sequence, and then add D*-weighting to this as the SIREDS sequence. The SE segment of the SIRES sequence is substituted by a gradient echo to produce the SIRGES sequence. This can have added to it diffusion weighting as the SIRDGES sequence.

The sixth group uses the same TI and subtracts a ps image from an m image once ($S^1IR$), or twice in the seventh group ($S^2IR$) with different Tis, for example, to selectively show a fluid or tissue.

(d) Divided IR (dIR) Sequences

A concern with division of IR sequences is the behavior of the $T_1$-filter if or when the denominator takes a value of zero. This potentially leads to infinite values of the filter. Even if zero values are avoided, there are values when the denominator approaches zero and division becomes unreliable as a result of noise and artifacts.

The problem can be largely avoided with two subtracted IR images by making the denominator the addition or sum of the signals in the two images. The $T_1$-filters have different Tis, and using magnitude reconstruction, the sum of them in the denominator is non-zero. Division also normalizes the sequence so that the effects of $□_m$ and $T_2$ are reduced or eliminated, as are those due to receiver coil inhomogeneity.

(e) $T_1$: Subtracted (SIR), Added (AIR) and Divided (dSIR) $T_1$-Filters (Univariate $T_1$ Models)

Figures 12A, 12B, 12C:
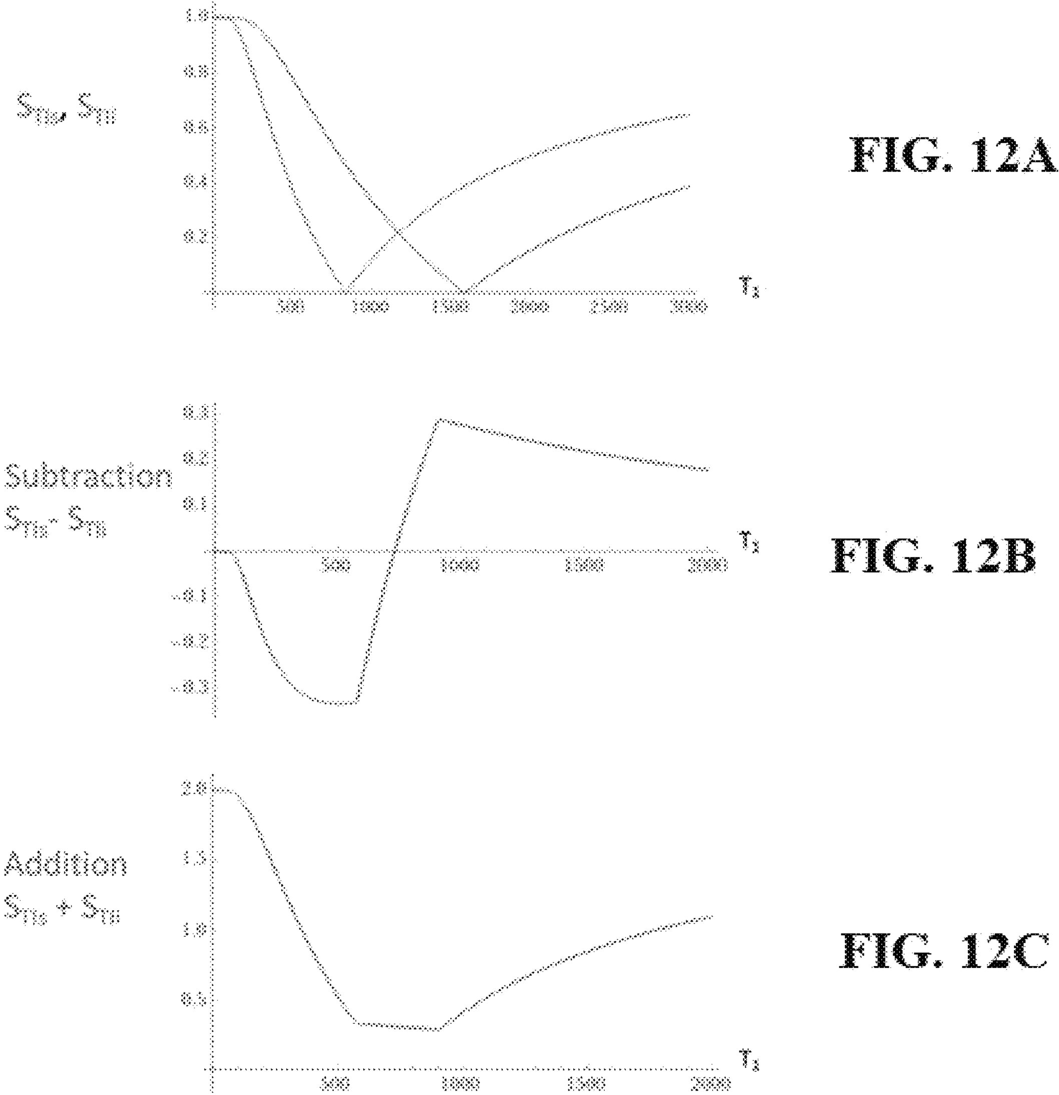
FIGS. 12A, 12B, and 12C illustrate SIR and AIR $T_1$-filters, according to one example.

Two IR $T_1$-filters with different Tis are shown in FIG. 12A. They are subtracted to give the SIR $T_1$-filter in FIG. 12B. This $T_1$-filter is steep in the X axis region between the inversion times, i.e. in the middle Domain (mD). The regions with shorter Tis than the mD is the lowest Domain (lD) and the region with longer $T_1$s is the highest Domain (hD). The two sequences in FIG. 12A can also be added as the Added IR (AIR) $T_1$-filter which is shown in FIG. 12C where there are higher signal and higher slopes outside of the mD. The mD in FIG. 12C has a nearly linear slightly downward sloping curve and a low signal.

FIGS. 12A, 12B, and 12C illustrate SIR and AIR $T_1$-filters. $T_1$ is shown along the X axis. FIG. 12A shows the TIs $T_1$-filter (pink) and $TI_i$ $T_1$-filter (blue), FIG. 12B shows the subtraction ($S_{Tis}-S_{Tii}$) IR or SIR $T_1$-filter, and FIG. 12C shows the addition ($S_{Tis}+S_{Tii}$) IR or AIR $T_1$-filter. In FIG. 12B, the slope of the curve in the mD is nearly double that of the $S_{Tis}$ $T_1$-filter (pink in FIG. 12A). In FIG. 12C, the signal at $T_1$=0 is doubled to 2.0, and the signal in the mD is reduced to about 0.35-0.33 in the nearly linear, slightly downward sloping central part of the AIR $T_1$-filter (i.e. the middle Domain, mD).

Figures 13A, 13B, 13C:
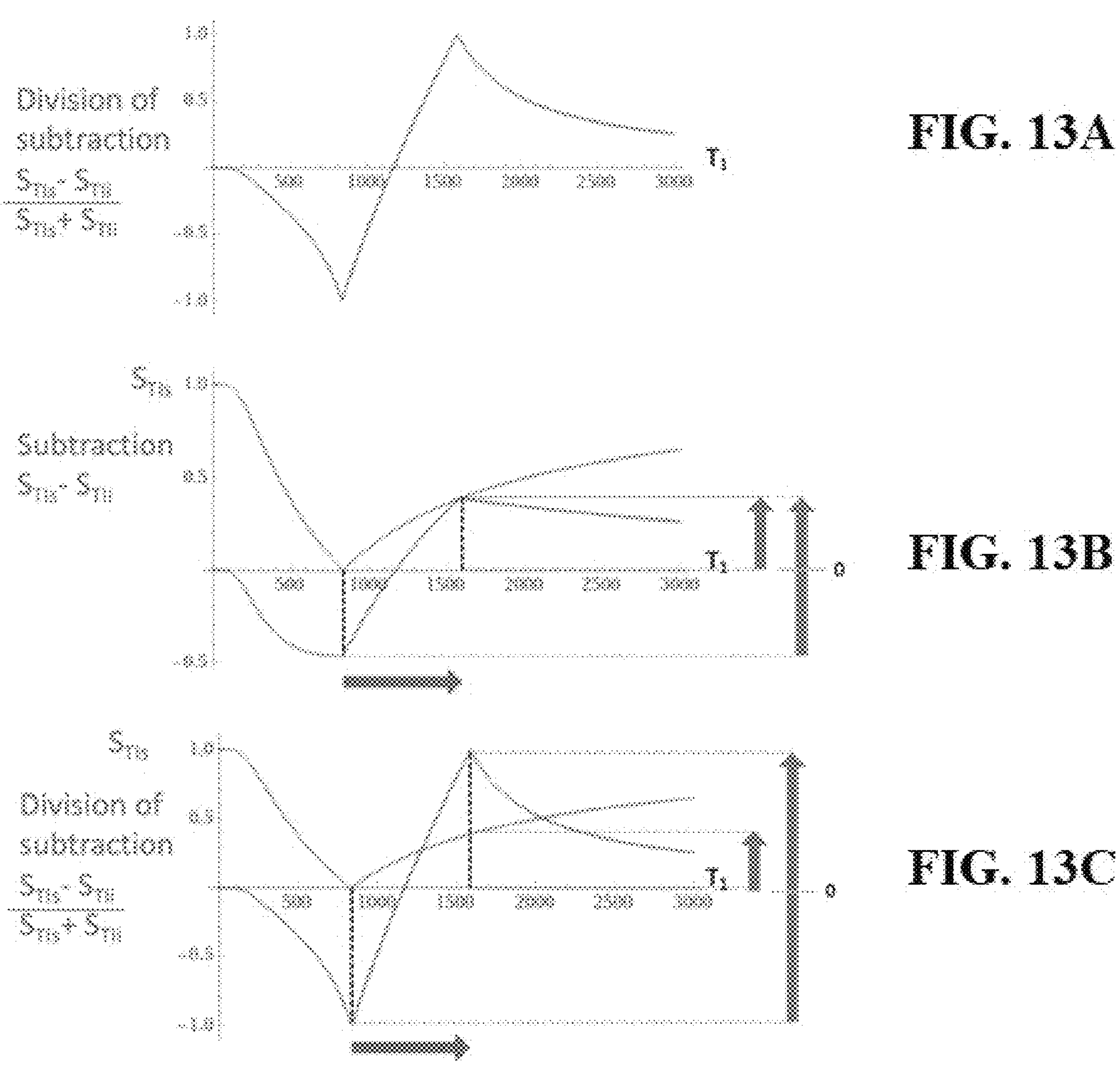
FIGS. 13A, 13B, and 13C illustrate dSIR $T_1$-bipolar filter and comparisons of the $S_{TIs}$ $T_1$-filter with the SIR $T_1$-filter, and of the $S_{TIs}$ $T_1$-filter with the dSIR $T_1$-bipolar filter for an increase in $T_1$ in the mD, according to one example.

FIG. 13A shows the divided Subtracted IR (dSIR) $T_1$-bipolar filter in which the SIR $T_1$-filter in FIG. 12B is divided by the AIR $T_1$-filter in FIG. 12C. The dSIR $T_1$-bipolar filter shows a very highly sloping positive mD.

FIGS. 13A, 13B, and 13C illustrate dSIR $T_1$-bipolar filter and comparisons of the $S_{Tis}$ $T_1$-filter with the SIR $T_1$-filter, and of the $S_{Tis}$ $T_1$-filter with the dSIR $T_1$-bipolar filter for an increase in $T_i$ in the mD. FIG. 13A shows division (d) of the subtraction ($S_{Tis}-S_{Tii}$) $T_1$-filter by the addition ($S_{Tis}+S_{Tii}$) $T_1$-filter to give $(S_{Tis}-S_{Tii})/(S_{Tis}+S_{Tii})$ or SIR/AIR=dSIR $T_1$-bipolar filter. FIG. 13B shows a comparison of the $S_{Tis}$ $T_1$-filter (pink) and the subtraction SIR $T_1$-filter (blue). FIG. 13C is a comparison of the $S_{Tis}$ $T_1$-filter (pink) with the divided subtraction dSIR $T_1$-bipolar filter (blue). The dSIR $T_1$-bipolar filter in FIG. 13A and FIG. 13C has maximum and minimum values of 1 and −1 respectively and is steeply sloping. In FIG. 13B, the increase in signal (i.e. contrast) for the increase in $T_1$ (horizontal green arrow) is about 0.35 for the $S_{Tis}$ $T_1$-filter and about 0.75 for the subtraction (SIR) $T_1$-filter. This represents an increase in contrast for the SIR $T_1$-filter compared to the $S_{Tis}$ $T_1$-filter of about two (right vertical arrows).

In FIG. 13C, the change in the $S_{Tis}$ $T_1$-filter is about 0.35 as shown also in FIG. 13B, and that in the divided subtraction dSIR $T_1$-bipolar filter is 2.0 representing an increase in contrast of about five times (right vertical arrows).

FIG. 13B compares the contrast from the short TI $T_1$-filter, $S_{Tis}$ (pink) which is that of a conventional intermediate $TI_i$ IR sequence such as MP-RAGE (Magnetization Prepared Rapid Acquisition Gradient Echo) to that from the SIR $T_1$-filter (blue). The vertical pink and blue arrows on the right show that the contrast produced by the SIR $T_1$-filter is about double that produced by the $S_{Tis}$ $T_1$-filter for the same change in $T_1$ (horizontal green arrow, $□T_1$).

FIG. 13C compares the contrast produced by the short TI $T_1$-filter, $S_{Tis}$ (pink) to that from the dSIR $T_1$-bipolar filter (blue). For the same change in $T_1$ (positive horizontal green arrow, $□T_1$) the dSIR $T_1$-bipolar filter generates about five times the contrast produced by the $S_{Tis}$ $T_1$-filter (vertical pink and blue arrows). As the second TI is moved closer to the first TI, the slope of the $T_1$-bipolar filter in the mD becomes steeper, and so the $T_1$ dependent contrast in the mD increases. This is documented in Table 2. In Table 2, as □TI decreases in magnitude from 90% to 13% the ratio of the contrast produced by the narrow mD dSIR $T_1$-bipolar filter to that produced by the conventional IR $T_1$-filter increases from 5 to 20. The mathematical basis for this is described in section 2.9 on $T_1$ mapping.

TABLE 2

| | | □TI | | $S_{Tis}$ | SdSIR | Ratio of SdSIR /$S_{Tis}$ |
|---|---|---|---|---|---|---|
| $TI_s$ (ms) | $TI_i$ (ms) | (ms) | % | contrast | contrast | contrast |
| 580 | 1100 | 520 | 90 | 0.40 | 2.0 | 5 |
| 580 | 840 | 260 | 45 | 0.25 | 2.0 | 8 |
| 580 | 710 | 130 | 22 | 0.15 | 2.0 | 13 |
| 580 | 655 | 75 | 13 | 0.10 | 2.0 | 20 |

Table 2 tabulates TIs, $TI_i$, □TI, $S_{Tis}$ contrast at $TI_i$, SdSIR contrast at $TI_i$, and Ratio of SdSIR/$S_{Tis}$ contrast. As $TI_i$ is reduced, the mD narrows, □TI decreases in magnitude and the signal for TIs at $TI_i$ ($S_{Tis}$ value) decreases. The ratio of the dSIR contrast to the $S_{TIs}$ contrast increases from 5 to 20, as □TI decreases in magnitude from 90% to 13% when the mD narrows.

Figures 14A, 14B, 14C:
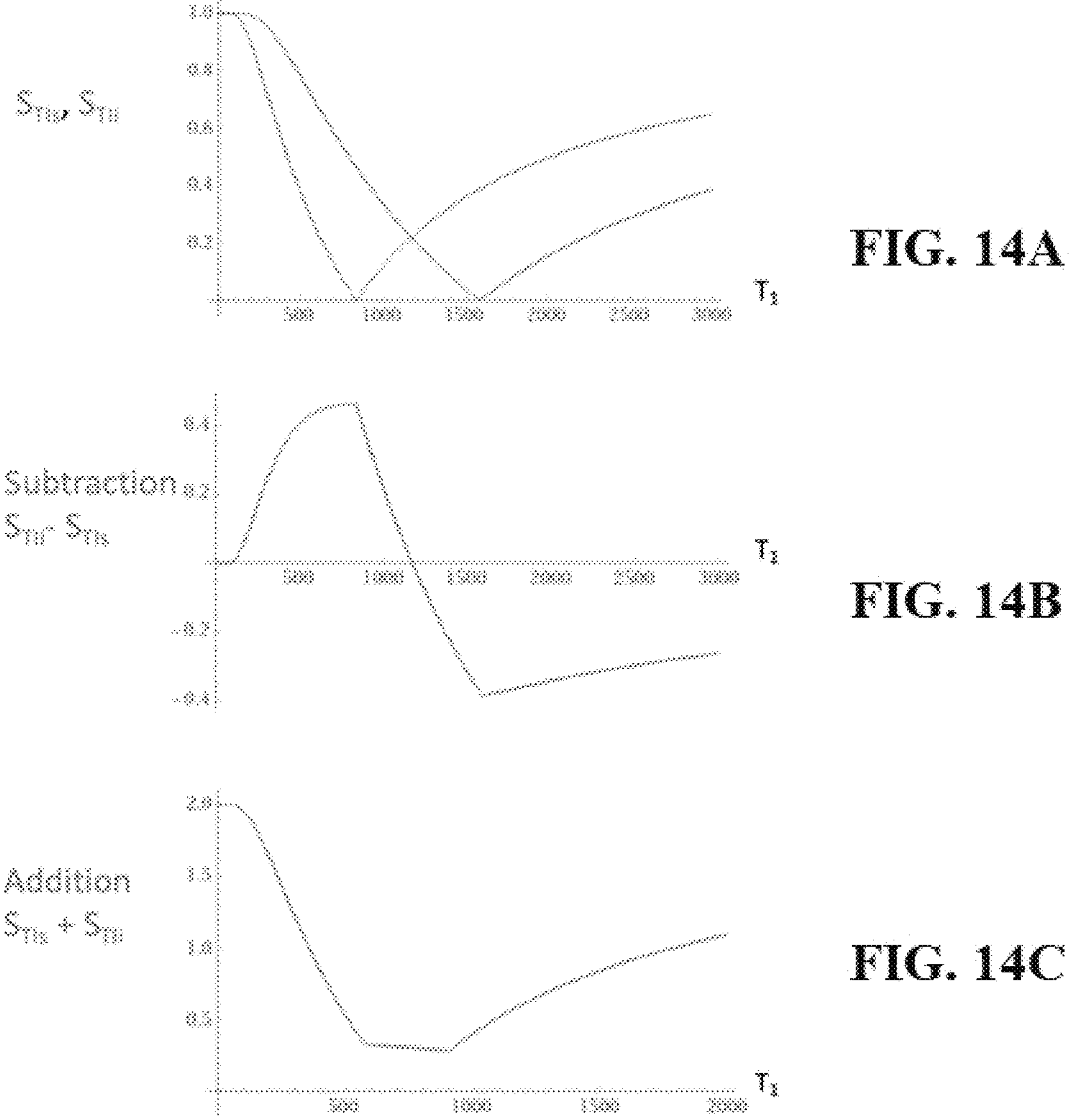
FIGS. 14A, 14B, and 14C illustrate rSIR and AIR $T_1$-filters filters, according to one example.

FIG. 14A illustrates the rSIR $T_1$-filter and shows the same two $T_1$-filters for $S_{TIs}$ and $S_{TIi}$ as in FIG. 12A. In FIG. 14B the reverse I subtraction rSIR $T_1$-filter is shown. This has a negative slope in the mD. In FIG. 14C addition of the two original $T_1$-filters gives the AIR $T_1$-filter as shown.

FIGS. 14A, 14B, and 14C illustrate rSIR and AIR $T_1$-filters. $T_1$ is shown along the X axis. FIG. 14A shows the TIs (pink) and $TI_i$ (blue) $T_1$-filters, FIG. 14B shows the subtraction ($S_{TIi}$−$S_{TIs}$) or reversed SIR, rSIR $T_1$-filter, and FIG. 14C shows the addition ($S_{TIs}$+$S_{TIi}$) or Added IR (AIR) $T_1$-filter. In FIG. 14B, the slope of the filter in the mD is negative and nearly double that of the $S_{TIi}$ $T_1$-filter. In FIG. 14C, the signal at $T_1$=0 is doubled to 2.0, and the signal in the mD it is reduced to about 0.38-0.36 as shown in the nearly linear slightly downward sloping central part of the AIR $T_1$-filter (i.e. the mD).

Figures 15A, 15B, 15C:
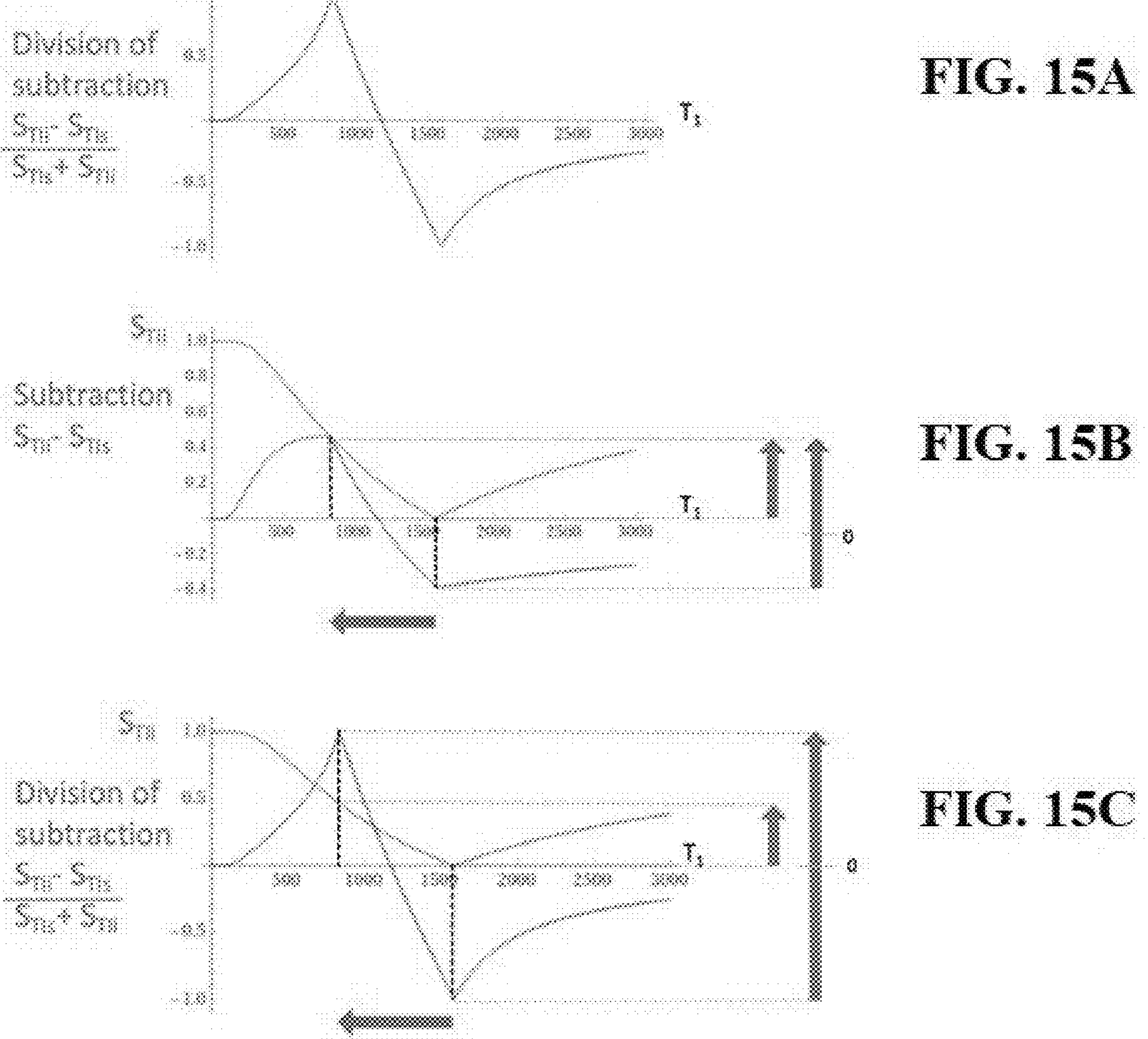
FIGS. 15A, 15B, and 15C illustrate rSIR $T_1$-filter and comparisons of the $S_T g$ $T_1$-filter with the SIR $T_1$-filter, and of the $S_T g$ $T_1$-filter with the drSIR $T_1$-bipolar filter for a decrease in $T_1$ in the mD, according to one example.

FIG. 15A shows the rSIR $T_1$-filter in FIG. 14B divided by the AIR $T_1$-filter in FIG. 14C to give the drSIR $T_1$-bipolar filter. This has a steeply sloping negative mD. FIG. 15B shows a comparison of the $S_{TIi}$ $T_1$-filter (pink) with the rSIR $T_1$-filter (blue) for a decrease in $T_i$ (negative horizontal green arrow, □$T_1$). The contrast produced by the rSIR $T_1$-filter is about twice that of the $S_{TIi}$ $T_1$-filter (vertical pink and blue arrows on right). FIG. 15C shows a comparison of the $S_{TIi}$ $T_1$-filter (pink) with the drSIR $T_1$-bipolar filter (blue). The contrast produced by the drSIR $T_1$-bipolar filter is about five times greater than that from the $S_{TIi}$ $T_1$-filter (pink and blue arrows on the right).

FIGS. 15A, 15B, and 15C illustrate rSIR $T_1$-filter and comparisons of the $S_{TIi}$ $T_1$-filter with the SIR $T_1$-filter, and of the $S_{TIi}$ $T_1$-filter with the drSIR $T_1$-bipolar filter for a decrease in $T_1$ in the mD. $T_1$ is along the X axis. FIG. 15A shows division (d) of the subtraction rSIR ($S_{TIi}$−$S_{TIs}$) $T_1$-filter by the addition (AIR) $T_1$-filter to give ($S_{TIs}$−$S_{TIi}$)/($S_{TIs}$+$S_{TIi}$) or rSIR/AIR=drSIR $T_1$-bipolar filter. FIG. 15B shows a comparison of the $S_{TIi}$ $T_1$-filter (pink) and the reverse subtraction rSIR $T_1$-filter (blue). FIG. 15C shows a comparison of the $S_{TIs}$ $T_1$-filter (pink) with the divided subtraction drSIR $T_1$ -bipolar filter (blue). The drSIR $T_1$-bipolar filter in FIG. 15A and FIG. 15C has maximum and minimum values of 1 and −1 respectively and is steeply sloping. In FIG. 15B, the increase in signal (i.e. contrast) for the decrease in $T_1$ from one end of the mD to the other (negative horizontal green arrow) is about 0.38-0.36 for the $S_{TIi}$ $T_1$-filter and about 0.85 for the reverse subtraction (rSIR) $T_1$-filter (vertical blue arrow). This represents an increase in contrast for the rSIR $T_1$-filter compared with the $S_{TIs}$ $T_1$-filter of nearly two (right vertical pink and blue arrows). In FIG. 15C the change in the $S_{TIi}$ $T_1$-filter for the same decrease in $T_1$ is about 0.38-0.36 as in FIG. 15B (vertical pink arrow), and that with the divided subtraction drSIR $T_1$-bipolar filter is 2.0 (vertical blue arrow) representing an increase in contrast of about five times.

The mathematical basis for selected aspects of the dSIR and drSIR $T_1$-bipolar filters including their near linearity, slope equal to +/−ln □/TI and high sensitivity to small changes in $T_1$ is included in section 2.9 on $T_1$ mapping.

(f) $□_m$, $T_1$, $T_2$ and D*: Subtracted, Added and Divided IR sequences (multivariate models)

The weighting of some TP-filters can be reversed to create sequences with synergistic contrast. Echo Subtraction (ES) can be used to reverse the $T_2$-weighting of the $T_2$-filter. This is accomplished by the subtraction: short TE $T_2$-filter minus long TE $T_2$-filter as in FIG. 16.

Figure 16:
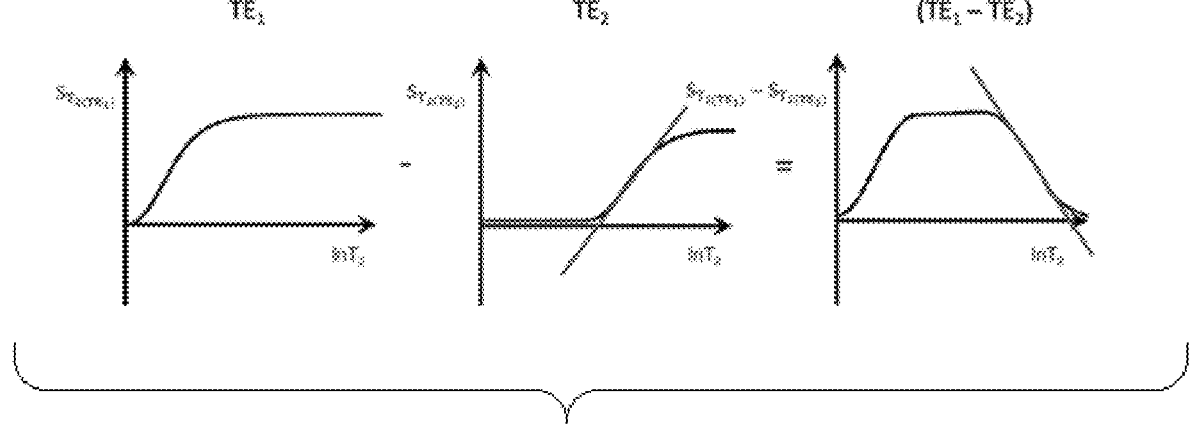
FIG. 16 illustrates a sequence including echo subtraction, according to one example.

FIG. 16 illustrates Echo Subtraction (ES). Short $TE_1$, long $TE_2$ and subtracted ($TE_1$−$TE_2$) $T_2$-filters. The positive slope of the $TE_2$ filter (red line) becomes negative with the ($TE_1$−$TE_2$) $T_2$-filter (red line).

Increases in $T_2$ in the chosen domain for the $T_2$-filter result in increased signal. For the ES $T_2$-filter, increase in $T_2$ results in decreased signal. Thus, the $T_2$-filter weighting is changed from positive to negative.

Figure 17:
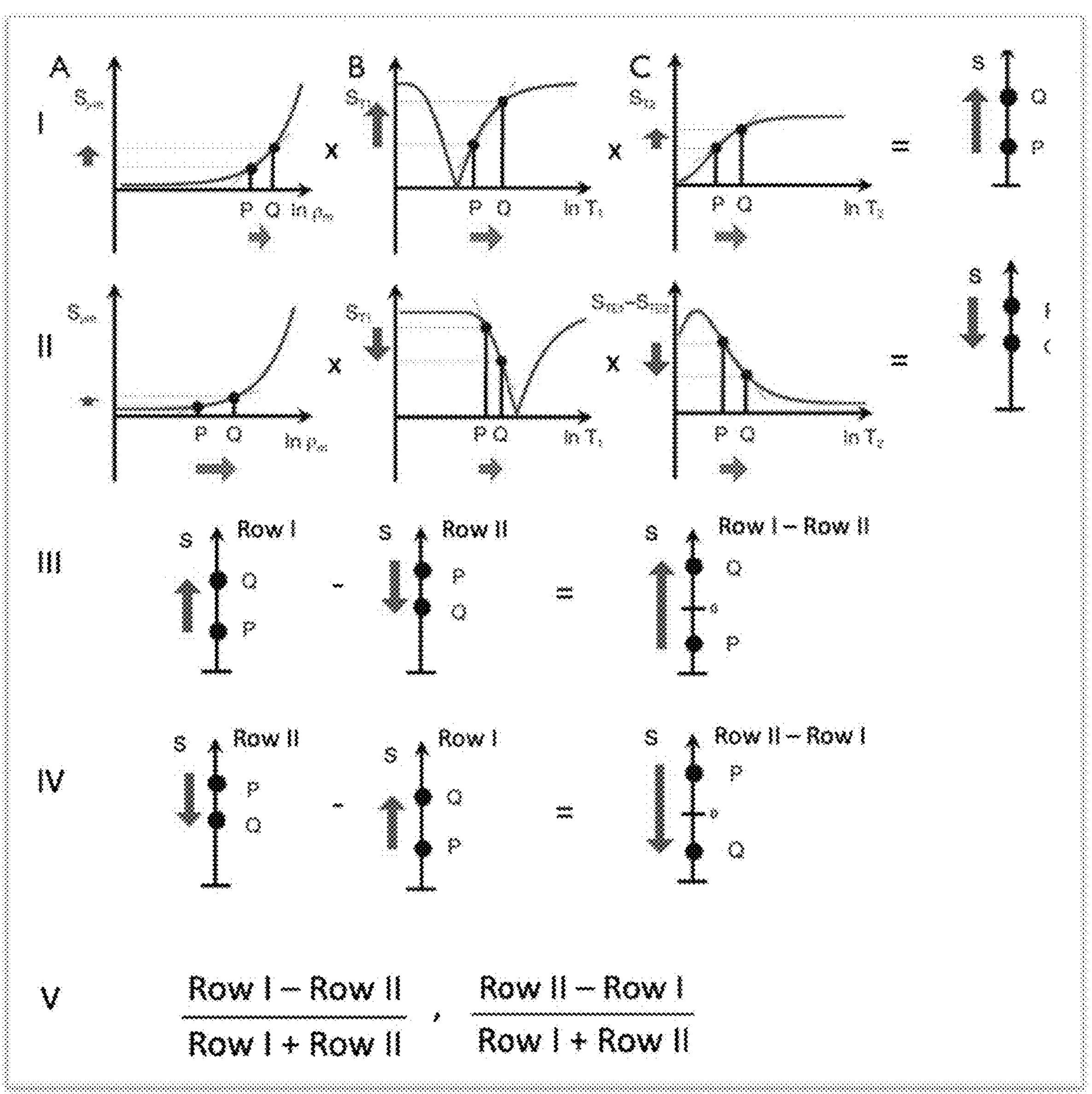
FIG. 17 illustrates a compilation of filters and resulting signals, according to one example.

FIG. 17 illustrates a compilation of filters and resulting signals. Row I of FIG. 17 illustrates a TP-filter with a short TI and a long TE resulting in positive contrast from the $T_1$- and $T_2$-filters (middle and right columns [B] and [C]). Row II of FIG. 17 shows an intermediate TI TP-filter with negative contrast from both the $T_1$- and $T_2$-filters. Row II includes the subtraction: intermediate $TI_i$ short TE sequence minus intermediate $TI_i$ long TE sequence. Thus, ES reverses the sign of the conventional $T_2$-filter. In Row III, the SIRES-filter is created by the subtraction: Row I minus Row II which produces overall synergistic positive $T_1$ and $T_2$ contrast. Row IV shows the reversed subtraction rSIRES. Row V shows the divided dSIRES and drSIRES TP-filters which result in further increase in $T_1$ contrast.

FIG. 17 illustrates SIRES TP-filters. Row I shows that increases in i m, $T_1$ and $T_2$ (green arrows) produce synergistic positive contrast (blue arrows). Row II (which includes ES) shows that increases in $T_1$ and $T_2$ produce synergistic negative contrast. In Row III, the subtraction (Row I minus Row II) results in synergistic positive contrast. In Row IV the reverse subtraction rSIRES TP-filter produces negative synergistic contrast. Row V shows the divided forms of the sequence dSIRES and drSIRES TP-filters which have increased $T_1$ contrast.

Diffusion Subtraction (DS) is used to reverse the weighting of the D*-filter. This is accomplished by the subtraction: D*-filter with b="0" minus D*-filter with a high b value as in FIGS. 18A, 18B, and 18C.

Figures 18A, 18B, 18C:
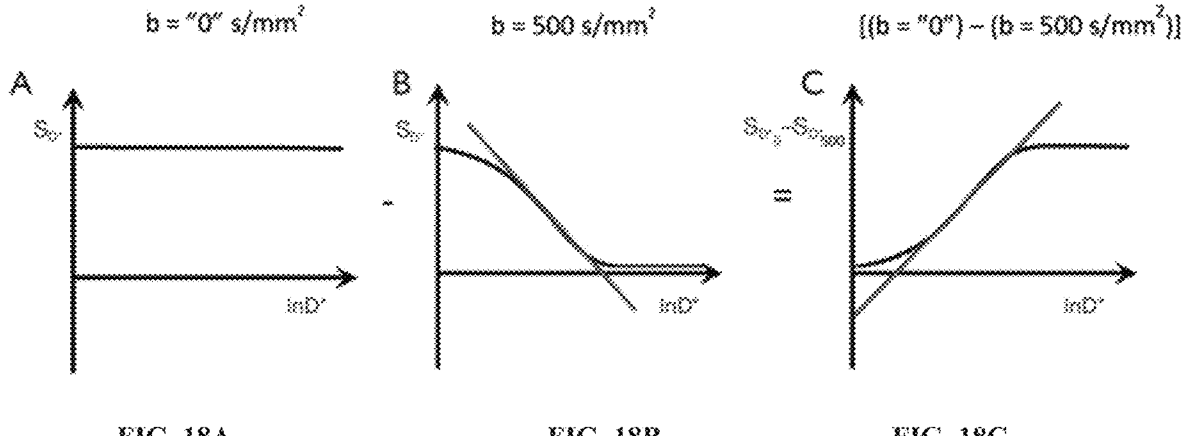
FIGS. 18A, 18B, and 18C illustrate a sequence of diffusion subtraction, according to one example.

FIGS. 18A, 18B, and 18C illustrate a sequence of Diffusion Subtraction (DS). B="0" s/mm$^2$ (FIG. 18A), b=500 s/mm$^2$ (FIG. 18B) and subtracted (b="0"−b=500 s/mm$^2$) (FIG. 18C) D*-filters. The negative sequence weighting in FIG. 18B becomes positive in FIG. 18C (red lines).

For the short TE and b="0" D*-filter in FIG. 18A, increase in D* results in no change. For the D*-filter in FIG. 18B, increase in D* results in negative contrast. For the subtracted D*-filter, increase in D* produces positive contrast.

Figure 19:
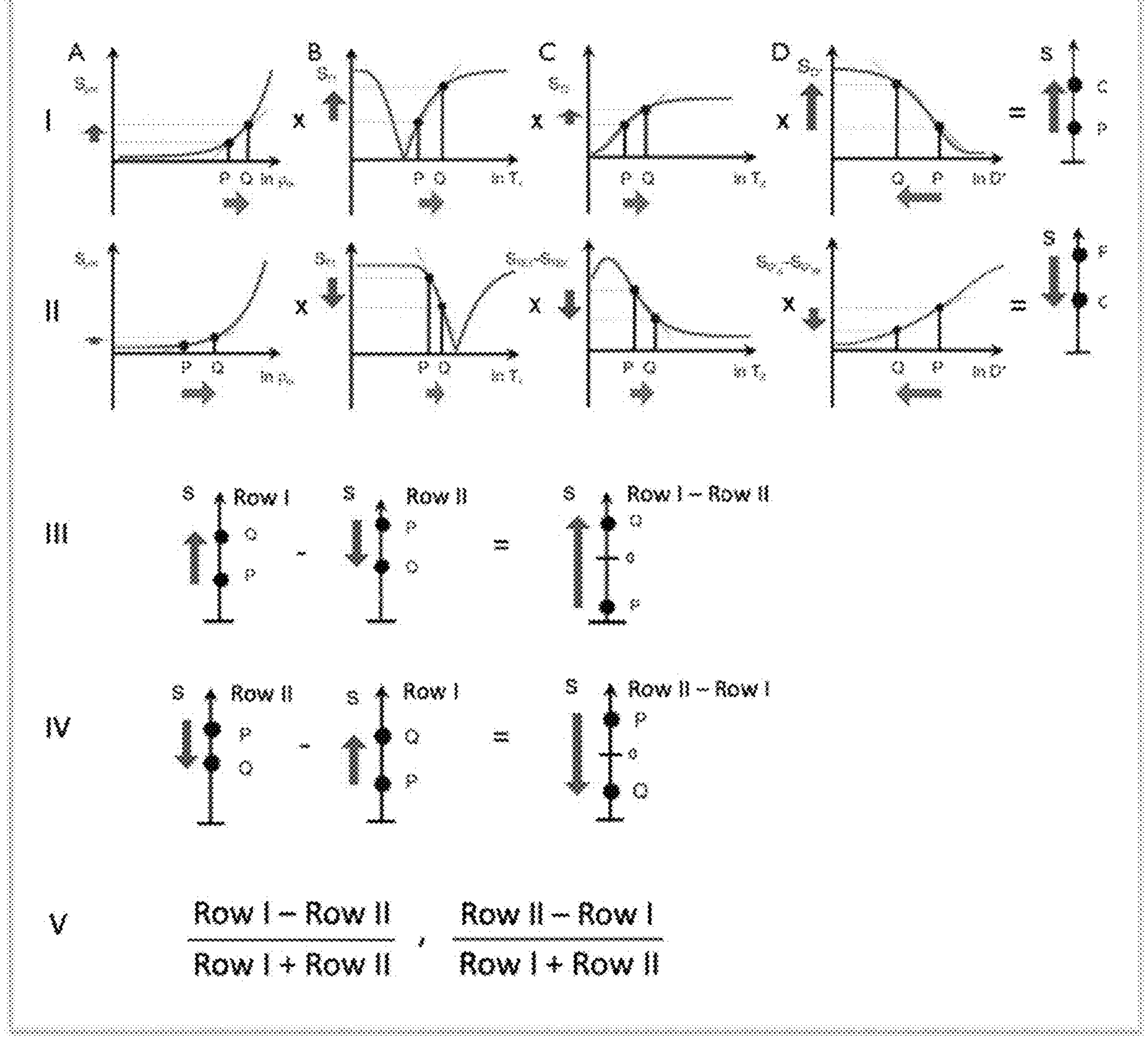
FIG. 19 illustrates a compilation of the SIREDS TP-filters, according to one example.

The SIREDS TP-filter (FIG. 19) adds D* to the SIRES TP-filter and includes DS to create synergistic $T_1$, $T_2$ and D* contrast. Row I in FIG. 19 is a TP-filter with a short Tis, long TE, and high b value resulting in positive synergistic contrast for increases in $T_1$ and $T_2$, and a decrease in D* as seen in some acute disease and many tumors. Row II in FIG. 19 is a TP-filter with negative synergistic contrast for increase in $T_1$ and $T_2$ and decrease in D*. Row II includes the subtraction: intermediate $TI_i$, short TE, b="0" D*-filter minus intermediate $TI_i$, short TE, high b value (i.e. ES and Diffusion Subtraction [EDS]). Row III shows the subtraction: Row I minus Row II to give the SIREDS TP-filter. Row IV shows the rSIREDS TP-filter. The dSIREDS and drSIREDS TP-filters are shown in Row V and increase $T_1$-weighting.

FIG. 19 illustrates a compilation of the SIREDS TP-filters. The $□_m$, $T_1$ and $T_2$ and D* contrasts are synergistic and positive in Row I, and the $T_1$, $T_2$ and D* contrasts are synergistic and negative in Row II. In Row III, the subtraction (Row I minus Row II) results in overall synergistic positive contrast. Row IV shows the reverse subtraction. Row V shows the divided forms of the TP-filters dSIREDS and drSIREDS which have increased $T_1$ contrast.

2.04 MASDEA Sequences

There are five groups of echo acquisition: (i) UTE/Zero Echo Time (U); (ii) Gradient Echo (G); (iii) Spin Echo (S); (iv) Pulsed Gradient Spin Echo diffusion weighted (D) and (v) Fat/Water (F/W). Each of these acquisitions can be multiplied, added, subtracted, and/or divided as shown in part in Table 3.

TABLE 3

MASDEA sequences

| Groups of MASDEA sequences | MASDEA sequences |
|---|---|
| EM | Echo Multiplication |
| EA | Echo Addition |
| EA-UG | Echo Addition-UG |
| EA-US | Echo Addition-US |
| EA-UD | Echo Addition-UD |
| EA-GS | Echo Addition-GS |
| EA-GD | Echo Addition-GD |
| EA-SD | Echo Addition-SD |
| ES | Echo Subtraction |
| ES-UG, rES-GU | Echo Subtraction-UG, reverse Echo Subtraction-GU |
| ES-US, rES-SU | Echo Subtraction-US, reverse Echo Subtraction-SU |
| ES-UD, rES-DU | Echo Subtraction-UD, reverse Echo Subtraction-DU |
| ES-GS, rES-SG | Echo Subtraction-GS, reverse Echo Subtraction-SG |
| ES-GD, rES-DG | Echo Subtraction-GD, reverse Echo Subtraction-DG |
| ES-SD, rES-DS | Echo Subtraction-SD, reverse Echo Subtraction-DS |
| Des | divided Echo Subtraction |
| dES-UG, drES-GU | divided Echo Subtraction-UG, divided reverse Echo Subtraction-GU |
| dES-US, drES-SU | divided Echo Subtraction-Us, divided reverse Echo Subtraction-SU |
| dES-UD, drES-DU | divided Echo Subtraction-UD, divided reverse Echo Subtraction-DU |
| dES-GS, drES-SG | divided Echo Subtraction-GS, divided reverse Echo Subtraction-SG |
| dES-GD, drES-DG | divided Echo Subtraction-GD, divided reverse Echo Subtraction-DG |
| dES-SD, drES-DS | divided Echo Subtraction-SD, divided reverse Echo Subtraction-DS |
| FWES | Fat Water Echo Subtraction |
| FWES-IO | Fat Water Echo Subtraction-In phase, Out of phase |

Abbreviations appearing in Table 3 include the following:

UTE/ZTE (ultrashort TE)=U

GE (gradient echo) (short TE)=G

SE (spin echo) (intermediate and long TE)=S

PGSE (pulsed gradient spin echo) (long TE and diffusion weighting)

=D

Fat (F)/water (W) in (I) and out of phase (O)=I, O

Figure 20:
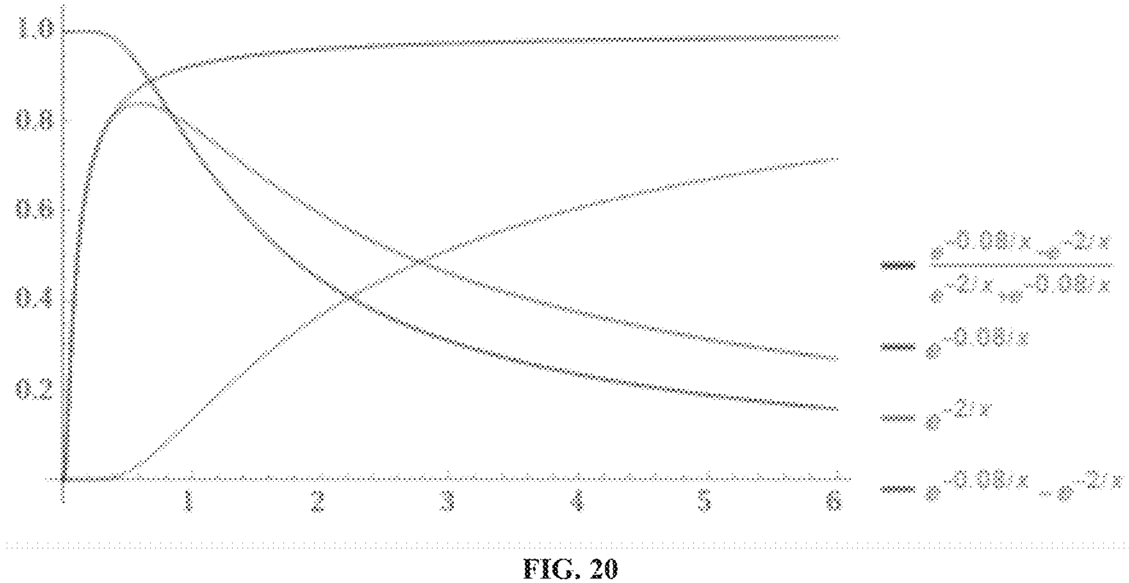
FIG. 20 illustrates a dES-UG $T_2$-filter, according to one example.

Echo subtraction of one acquisition from another is a $T_2$-filter of interest. Addition of two echo acquisitions can be used to divide subtractions to produce divided (d) forms of the MASDEA sequences. This is illustrated in FIG. 20 where plots of a UTE $T_2$-filter (pink) and gradient echo $T_2$-filter (yellow) are shown. ES-UG is shown (green) and dES-UG (blue). For ultrashort TEs of 0.3 ms or less the ES-UG $T_2$-filter starts at zero and increases to a maximum of about 0.3 ms whereas the dES-UG $T_2$-filter has a value of 1 at $T_2$=0 ms and shows high signal up until TE=0.3 ms. This translates into good performance for ultrashort $T_2$ tissues in the 0 to 0.3 ms range such as cortical bone, calcified tissues, myelin, lung, and some iron containing tissues.

FIG. 20 illustrates a dES-UG $T_2$-filter. Plots of UTE (pink), gradient echo (yellow), ES-UG (green) and dES-UG (blue) signals vs $T_2$ in ms. The ES-UG $T_2$-filter (band pass) (green) increases from 0 at $T_2$=0 to a maximum at about 0.3 ms. The dES-UG $T_2$-filter (low pass) (blue) shows a high signal at TE=0 ms and this decreases at about 0.2 ms. It provides a more consistent performance for $T_2$s in the 0-0.3 ms domain.

2.05 Synergistic Contrast MRI (scMRI)

2.05.1 Definition of Synergistic Contrast MRI (scMRI)

Synergistic contrast can arise in two main ways:

(i) A single TP can be used twice or more in a sequence. For example, $T_1$ can be used in the $T_1$ dependent TR segment of an IR sequence as well as the $T_1$ dependent TI segment. $T_1$ is also used twice in DIR sequences when two TI segments are multiplied together, and in the Subtracted IR (SIR) sequence when using the subtraction: short TIs segment minus intermediate $TI_i$ segment. The synergistic $T_1$ contrast from the SIR sequence can be increased further by using $T_1$ 3-4 times in the form of dSIR and drSIR sequences.

Synergistic contrast may arise from repeated use of $T_2$ when imaging ultrashort $T_2$ tissues with an IR sequence using a long adiabatic inversion pulse to invert and null long $T_2$ signals while ultrashort $T_2$ tissues that are saturated by the inversion pulse recover, and following this after the 90° excitation pulse by ES. The two effects, firstly from the inversion pulse and nulling, and secondly from the decay in transverse magnetization produce synergistic negative contrast when there is an increase in $T_2$ in ultrashort $T_2$ tissues.

(ii) Two or more different TPs can also be used to produce synergistic contrast. Clinical pulse sequences have a structure including $\rho_m$-, $T_1$- and $T_2$-filters as seen in SE sequences. There are additional options which can be added such as those for $T_1$ dependent inversion pulses and D* sensitization. In some circumstances $\rho_m$ is a minor determinant of contrast and $T_1$, $T_2$, and D* are major determinants. The most common change in TPs in disease is concurrent increases in $\rho_m$, $T_1$, $T_2$. In this situation with the SE sequence, the contrast developed by an increase in $T_1$ is negative while that developed by an increase in $T_2$ is positive, so that simultaneous increases in $T_1$ and $T_2$ produce opposed contrast and the net, or overall, contrast is reduced. To avoid this problem, $T_1$-weighted sequences use a short TE to minimize the opposed $T_2$ contrast, and $T_2$-weighted sequences use a long TR to minimize the opposed $T_1$ contrast. The dominant source of contrast in the resulting sequences is then a single TP i.e., $T_1$ or $T_2$ and the sequences are described as $T_1$-weighted or $T_2$-weighted respectively. They are not synergistic for $T_1$ and $T_2$ contrast.

In particular circumstances, such as certain forms of the STIR and the DIR sequences, the $T_1$ contrast produced by an increase in $T_1$ is positive, and so is the $T_2$ contrast produced by an increase in $T_2$. The effects of the concurrent increases in $T_1$ and $T_2$ are therefore synergistic and typically result in high positive lesion contrast.

The contrast produced above from (i) a single TP, or (ii) two or more different TPs can be supplemented by increasing or decreasing signals from certain normal tissues and/or fluids. There may be little contrast between high signal lesions and high signal fat, long $T_2$ tissues, or fluids. Reduction in the normal signal from these latter tissues or fluids (using the same or different TPs as those used to create the original synergistic contrast in (i) and/or (ii)) can increase the contrast between the high signal lesions and the zero or low signal suppressed tissues and/or fluids. It may also result in a more appropriate dynamic range for the image.

In a tissue with a mixture of ultrashort $T_2$ and long $T_2$ tissues, for example, low abundance ultrashort $T_2$ tissues may only become apparent if the more abundant signals from the long $T_2$ tissues are reduced or suppressed. This also applies to edema in yellow bone marrow, where suppression of the more abundant fat signal may show the lower concentration edema. Signals can also be increased for the same purpose.

The synergistic contrast produced in (i) and (ii) can also be supplemented by opposed contrast outside the region of interest.

One or both of mechanisms (i) and (ii) described above may be used in any one synergistic contrast sequence with, or without, supplementary synergistic contrast from suppression or increase of signals from normal tissues as well as the use of opposed contrast. Achievement of synergistic contrast requires a knowledge of the sign of sequence weighting of the TP-filters involved, as well as the sign of the change in each TP.

2.05.2 Image Processing to Achieve Synergistic Contrast

There are three situations within sequences where the ability to reverse the sign of the weighting of a TP-filter of the sequence is important for achieving synergistic contrast. These are firstly, reversal of the sign of the $T_1$ contrast produced by a change in $T_1$ with IR sequences by using different Tis (together with m reconstruction). Secondly, reversal of the sign of $T_2$ contrast produced by a change in $T_2$ with SE $T_2$-filter by the subtraction: shorter TE $T_2$-filter minus longer TE $T_2$-filter i.e., ES. Thirdly, reversal of the sign of diffusion contrast produced by the PGSE D*-filter using the subtraction: low b value (e.g. 0-20 s/mm$^2$) D*-filter minus high b value (e.g. 500-1500 s/mm$^2$) D*-filter i.e. DS. This ability to change the sign of the sequence TP-filter and the resulting contrast for $T_1$, $T_2$ and D* permits creating synergistic contrast from either positive or negative changes in each of $T_1$, $T_2$ and D*in disease.

In addition to changing the sign of the sequence weighting of a TP-filter within a sequence as above, the order of subtraction of two sequences can be reversed, and so reverse the contrast produced by the sequences. This is reverse I subtraction.

Using the same change in a TP twice or more in the same sequence may result in higher synergistic contrast than just using it once. Using changes in different TPs may also be effective in increasing overall contrast. This is because $T_1$, $T_2$ and D* often change concurrently in disease and using synergistic contrast to exploit the lesion contrast developed by each of these TPs may result in higher overall contrast. These are approaches targeted at increasing sequence sensitivity.

Synergistic contrast can also be used to improve sequence specificity, for example, by using the reductions in both $T_1$ and $T_2$* produced by organic iron to provide high contrast visualization of its effects.

2.06 Targeted MRI (tMRI)

MRI examinations are targeted. Whole body MRI includes sequences sensitive to only a few TPs (Table 4).

TABLE 4

Levels of targeting of MRI examinations.

| # | Target |
|---|---|
| 1. | Whole body |
| 2. | Region e.g., head, thorax |
| 3. | Organ or physiological system e.g., brain, CNS |
| 4. | Tissue or tissue components e.g., white matter, myelin water, short $T_2$ components |
| 5. | Tissue or tissue component property e.g., $T_1$, $T_2$ |
| 6. | Sign of change in tissue property |
| 7. | Size of change in tissue property |

The term targeted MRI (tMRI) can be applied to sequences focused on specific tissues, their TPs and changes in these TPs in disease (e.g., #4-7 in Table 4). This is greater targeting than that of typical conventional $T_1$-wSE and IR sequences in which there is sensitivity to changes in $T_1$ over a relatively broad $T_1$ domain as shown by the slopes of their $T_1$-filters. They have a maximum slope centrally but lesser slopes extending out on either side to flat plateaus at low and high values of $T_1$ where there is less sensitivity to changes in $T_1$ (see FIGS. 3 and 7). Narrow mD dSIR and drSIR sequences are highly sensitive to small changes in $T_1$ in the mD (see FIGS. 13C and 15C). dSIR and drSIR $T_1$-bipolar filters are generally less sensitive to changes in $T_1$ outside of the mD. Larger changes in $T_1$ in the domains outside of the mD may be usefully shown with conventional sequences.

In dSIR and drSIR imaging, as □$T_1$ decreases, □TI is decreased to match it (as part of tMRI) and contrast amplification increases correspondingly. As a result, contrast is maintained in spite of the decrease in □$T_1$ up until the point that images become noise and/or artefact limited. This makes dSIR and drSIR images particularly suited to imaging small changes in $T_1$.

Decreases in $T_1$ may be produced by Gadolinium Based Contrast Agents (GBCAs) using the mD of drSIR sequences and these can be used to produce positive contrast in the mD of drSIR sequences. The level of contrast enhancement may be ten or more times greater than with conventional IR sequences such as MP-RAGE. These changes apply to fluids such as blood and CSF as well as to tissues.

In addition, decreases in $T_1$ produced by GBCAs can be shown using the highest Domain (hD) of dSIR sequences.

Magnetic iron oxide particles (MIOPs) may be used to produce both a reduction in $T_1$ and $T_2$* and these effects may be detected with drSIR sequences using a $T_2$* data acquisition, where both the reductions in $T_1$ and $T_2$* produce synergistic positive contrast.

dSIR images can also be targeted at perfusion. This can be done by targeting changes in $T_1$ when inverted longitudinal magnetization blood flows into an uninverted longitudinal magnetization slice resulting in an increase in observed $T_1$ in the slice, or when uninverted longitudinal magnetization blood flows into an inverted longitudinal magnetization slice and produces a decrease in observed $T_1$ with dSIR and drSIR sequences. This perfusion effect can be coupled with changes in $T_2$* associated with the Blood Oxygen Level Dependent (BOLD) effect to produce contrast in functional MRI (fMRI).

The presence of paramagnetic molecular $O_2$ in fluids and tissues results in a reduction in $T_1$. This change may be amplified with drSIR images to produce high contrast.

In both non-contrast angiography and contrast angiography with GBCAs, reductions in $T_1$ are produced. These can also be amplified using drSIR sequences.

2.07 Contrast at Tissue Boundaries

In other sections, contrast between two voxels has been considered. Consider next the space between voxels, or contrast at boundaries between two voxels.

In general terms, contrast detectability at boundaries between two voxels can be related to $C_{ab}=\square S$ or $C_{fr}=\square S/S$ divided by the distance □x between the voxels. Boundaries are more detectable when contrast is high and □x is low, rather than in the opposite situation where contrast is low and □x is high.

At a boundary between two pure tissues P and Q it is useful to define the tissue fraction f which is the proportion of the second tissue Q in a voxel containing a mixture of both tissues. The proportion of the other tissue P is then (1−f).

The $T_1$ of the mixture of the two tissues (P and Q) can be expressed as a function:

$$T_{1P,Q}=\Gamma(T_{1P},T_{1Q},f) \quad [13]$$

where $T_{1P,Q}$ is the $T_1$ of the mixture, $T_{1P}$ is the $T_1$ of P, and $T_{1Q}$ is the $T_1$ of Q. An example of this is shown in FIG. 21 (upper row, column B).

Figure 21:
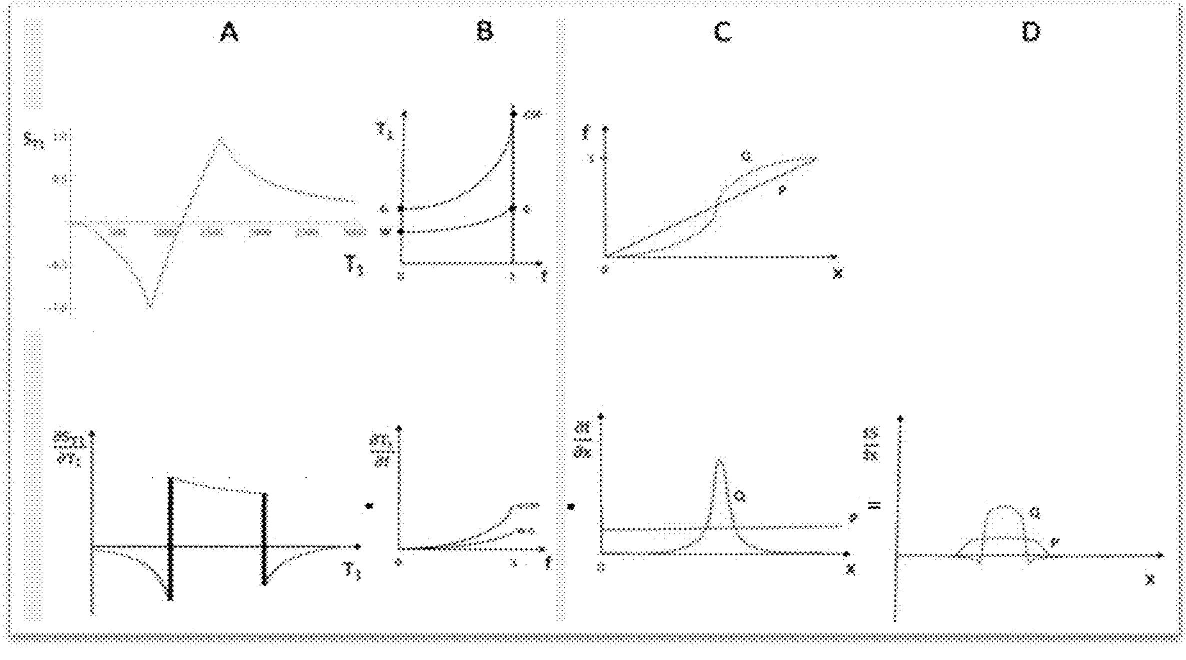
FIG. 21 illustrates fractional contrast between two tissues e.g. white and gray matter over distance x, according to one example.

FIG. 21 illustrates fractional contrast between two tissues e.g. white and gray matter over distance x. In the upper row in column A is the $T_1$-filter of the sequence, in column B is the $T_1$ of the mixture of the two tissues plotted against tissue fraction f, and in column C is f plotted against distance x. In the lower row the partial derivatives of each of these functions are shown. The contrast with distance $$\frac{dS}{dx}$$

is the product of the three partial derivatives in columns A, B and C and is shown in column D on the right.

It is also useful to consider □∂f/∂x the change in tissue fraction with distance x. This is shown in FIG. 21 (upper row, column C) and may be gradual corresponding to a low value of $$\frac{\partial f}{\partial x}(P)$$

or more abrupt in parts corresponding to higher values of $$\frac{\partial f}{\partial x}(Q).$$

Using the chain rule from differential calculus, for $T_1$ $$\frac{1}{S_{T1}}\cdot\square\frac{\Delta S}{\Delta x}\approx\frac{1}{S_{T1}}\cdot\frac{dS}{dx}=\frac{1}{S_{T1}}\cdot\frac{\partial S_{T1}}{\partial T_1}\cdot\frac{\partial T_1}{\partial f}\cdot\frac{\partial f}{\partial x} \quad [14]$$

where $$\frac{1}{S_{T1}}\cdot\square\frac{\Delta S}{\Delta x}$$

is the change in fractional contrast with distance x, $S_{T1}$ is the $T_1$-filter signal, $$\frac{dS}{dx}$$

is a measure of detectable contrast, $$\frac{\partial S_{T1}}{\partial T_1}$$

is the first partial derivative of $S_{T1}$ with respect to $T_1$ i.e. the sequence $T_1$-weighting, $$\frac{\partial T_1}{\partial f}$$

is the change in $T_1$ with tissue fraction f, and $$\frac{\partial f}{\partial x}$$

is the change in f with distance x. This is illustrated in FIG. 21 (lower row).

If the sequence weighting is high as within the mD of a dSIR sequence $$\frac{\partial S_{T1}}{\partial T_1}$$

is high (Table 5). In the brain $$\frac{\partial T_1}{\partial f}$$

is increased from white-gray matter to gray of matter-CSF to white matter-CSF at boundaries between tissue fluids.

$$\frac{\partial f}{\partial x}$$

increases as the transition from one tissue changes from gradual to abrupt.

TABLE 5

| $\frac{\partial S_{T1}}{\partial T_1}$ i.e. sequence weighting = slope of $T_1$-filter | $\frac{\partial T_1}{\partial f}$ | $\frac{\partial f}{\partial x}$ |
|---|---|---|
| Increasing $T_1$ sequence weighting from upper row to lower row (below) | Increasing value from upper row to lower row (below) | Increasing value from upper row to lower row (below) |
| SGE | White- gray matter | Gradual |
| IR | gray matter-CSF | Abrupt |
| SIR | White matter-CSF | |
| dSIR | | |

Table 5 illustrates partial derivatives $$\frac{\partial S_{T1}}{\partial T_1}, \frac{\partial S_{T1}}{\partial f}$$

and $$\frac{\partial f}{\partial x}$$

which determine $T_1$-dependent change in signal or contrast with distance at boundaries.

If one or more of the partial derivatives in Eq. [14] is zero, the tissue appears flat on the image. This can occur with "dark bone" imaging where the SGE sequence has a low flip angle and short TE, and is insensitive to $T_1$ changes so that $$\frac{\partial S_{T1}}{\partial T_1} = 0$$

(but not to low □$_m$ which accounts for the bone contrast). If the $T_1$s of P and Q are the same $$\frac{\partial T_1}{\partial f} = 0,$$

then no contrast results. If $$\frac{\partial f}{\partial x} = 0$$

i.e. there is no change in the proportions of the two tissues, no contrast results.

At a boundary between two tissues the actual $T_1$ of the voxels with mixtures of tissues within them spans the range of $T_1$ values between the two tissues. This is shown in FIG. 22.

Figure 22:
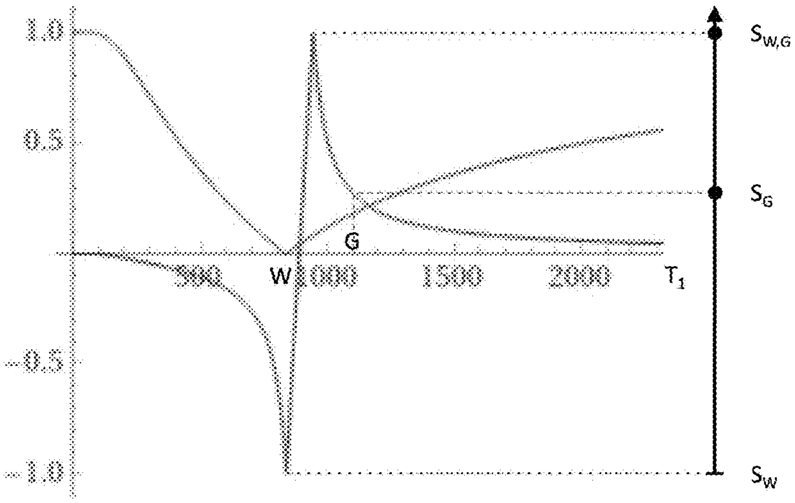
FIG. 22 illustrates a dSIR $T_1$-bipolar filter with a narrow mD, according to one example.

FIG. 22 illustrates a dSIR $T_1$-bipolar filter with a narrow mD extending from white matter (W) to a $T_{1W,G}$ between white matter and gray matter (G) (blue), and a white matter nulled $T_1$-filter e.g. from MP-RAGE (pink). The peak signal ($S_{W,G}$) appears between W and G in the X axis where there are partial volume effects producing the $T_{1W,G}$ between W and G matter corresponding to the peak signal $S_{W,G}$. This results in a high signal line between white and gray matter as shown in FIG. 23.

Figure 23:
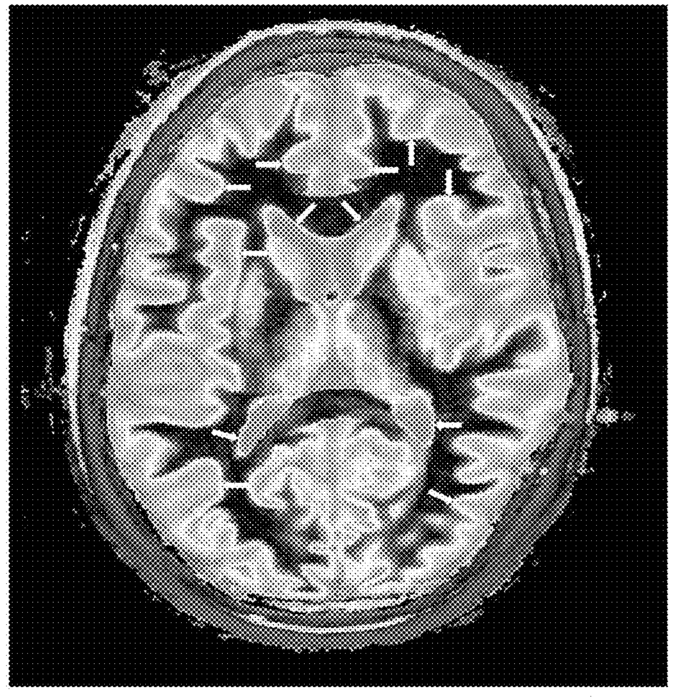
FIG. 23 illustrates an image having a high signal line between white and gray matter, according to one example.

If the $T_1$-filter is such that a $T_1$ value between those of the two tissues results in a high value of S, a high signal line results at the boundary between the two tissues, as seen in FIG. 23.

FIG. 23 illustrates a dSIR image with the first TI nulling white matter (W) and the second TI less than that needed to null gray (G) matter. High signal boundaries are seen between W and G matter as well as between white matter and CSF (arrows).

The high signal boundary at the white matter gray matter boundary inside the brain in FIG. 23 was obtained using a narrow mD.

FIG. 24 shows use of a wide mD $T_1$-bipolar filter in which maximum signal is reached with a $T_1$ between those of gray matter and CSF.

FIG. 24 illustrates a dSIR $T_1$-bipolar filter (blue filter) with the first TI nulling white matter (W) and a wide mD with the second TI nulling at a $T_{1G,CSF}$ greater than the $T_1$ of gray matter (G) corresponding to a mixture of gray matter and CSF. The pink $T_1$-filter is that from a white matter nulled IR sequence e.g. MP-RAGE. The signal $S_{G,CSF}$ is greater than that of the signal from gray matter $S_G$ and that from white matter $S_W$, and corresponds to the line between gray matter and CSF seen outside of the brain in FIG. 25.

This arises from partial volume effects between gray matter and CSF, and produces a high signal boundary between gray matter and CSF outside of the brain as shown in FIG. 25.

FIG. 25 illustrates a dSIR image of the brain using a wide mD with the second TI longer than that needed to null cortical gray matter ($TI_s$=350 ms and $TI_l$=800 ms, □TI=130% at 3T). High signal boundaries are seen outside of the brain between the cortex and CSF (arrows).

The width and location of the boundary e.g. white matter gray matter or gray matter CSF can be changed by choice of mD. The width of the boundary can be changed by altering the slope and location of the maximum signal of the $T_1$-filter. In general, a wider mD results in greater width of tissue boundaries.

High signal boundaries provide a useful basis for locating lesions as well as for segmentation of tissues and following changes in space in serial imaging studies as described in the next section.

2.08 Small Change Regimes

2.08.1 Single Imaging Studies

In general terms, there is often no particular premium in clinical MRI in making existing high contrast due to large changes in TPs even greater, since the abnormalities are already obvious. As a result, one emphasis with MASDIR sequences is on demonstrating lesions with high contrast where there are only small changes in TPs which are insufficient to produce useful contrast with conventional imaging. Ultra-high contrast imaging regimes can be tailored to monitor changes over time and follow their natural history, and/or the effects of treatment.

Increased sensitization in the mD is accompanied by a decreased width of the mD. This combination is particularly appropriate for detecting small changes in $T_1$ in specific tissues where high contrast amplification can be applied to small changes in $T_1$. Small changes in $T_1$ and $T_2$ from normal are commonly seen in earlier and more subtle forms of disease.

On MR images, changes may be in signal or contrast, and in space e.g. increase or decrease in size of normal structures, or in both signal/contrast and space. Differences/changes in signal may be anatomical on single images, but may also include changes in space with growth and atrophy for example.

Disease usually involves both changes in signal and space, but in some cases the changes in space are small and the situation can be treated as a change in signal.

2.08.2 Serial Studies

The changes in signal and space from normal in a single image may change over time in serial studies as part of the natural history of the disease and/or the result of therapy. In a situation where changes are small, rigid body registration is well suited to accurately aligning images obtained on two or more occasions so that genuine changes can be distinguished from artefactual differences due to variation in slice alignment.

Isotropic SGE sequences and a system of interpretating images (including distinguishing pure signal changes from spatial changes) can be used. MASDIR sequences using MP-RAGE/BRAVO (BRAain Volume) type data acquisitions with SIR/rSIR and or dSIR/drSIR image processing offer increased sensitivity to changes in contrast. A MASDIR sequence can provide high signal and high contrast definition of boundaries to improve detection of changes in space.

2.08.3 Magnetization Transfer (MT)

Magnetization transfer (MT) results in a reduction in observed mobile proton density as well as a corresponding reduction in observed $T_1$. In disease, there may be less MT effect and so a smaller decrease in $T_1$ compared with normal tissue. The net result is an increase in observed $T_1$ in the diseased tissue relative to the $T_1$ of normal tissue. This may be synergistic with an increase in $T_1$ in tissue due to disease.

2.09 $T_1$ Mapping

The signals $S_s$ and $S_i$ for two long TR IR magnitude $T_1$-filters with short and intermediate Tis ($TI_s$ and $TI_i$) as shown in FIGS. 12A and 14A are respectively given by:

$$S_s = 1 - 2e(-TI_s/T_1) \quad [15]$$

and $$S_i = 1 - 2e(-TI_i/T_1) \quad [16]$$

Performing the subtraction: magnitude of the IR signal $|S_s|$ in Eq. [15] minus magnitude of the IR signal $|S_i|$ in Eq. [16] gives the signal of the SIR $T_1$-filter $S_{SIR}$ which is equal to $-S_s-S_I$ i.e.:

$$S_{SIR} = 2e(-TI_s/T_1) + 2e(-TI_i/T_1) - 2 \quad [17]$$

Addition of the magnitudes of the two IR signals $|S_s|$ and $|S_i|$ in Eqs. [15] and [16]$S_{AIR}$ is equal to $-S_s+S_I$ i.e.:

$$S_{AIR} = 2e(-TI_s/T_1) - 2e(-TI_i/T_1) \quad [18]$$

Division of the signal of the subtraction $T_1$-filter $S_{SIR}$ in Eq. [17] by the signal of the addition $T_i$-filter $S_{AIR}$ in Eq. [18] gives the signal of the $S_{dSIR}$ $T_1$-filter:

$$S_{dSIR} = \frac{e(-TI_s/T_1) + e(-TI_i/T_1) - 1}{e(-TI_s/T_1) - e(-TI_i/T_1)} \quad [19]$$

This expression can be recharacterized to provide insight into the properties of the dSIR $T_1$-filter. To do this, a linear equation of the form y=mx+c between the end points of the mD can be produced by fitting a straight line between the first and last points of the mD (i.e. first point x=$TI_s$/ln 2 and y=−1, and last point x=$TI_i$/ln 2 and y=+1). It is an approximation to the dSIR $T_1$-filter in the mD so $S_{dSIR}$ in the mD is given by:

$$S_{dSIR} \approx \frac{\ln 4}{\Delta TI} T_1 - \frac{\sum TI}{\Delta TI} \quad [20]$$

where $\Delta TI = TI_i - TI_s$ (i.e., longer TI minus shorter TI which is positive) and $\tau TI = TI_s + TI_i$. The convention for □TI is to define it by the subtraction: second TI minus first TI. □TI may be positive or negative. The offset is negative.

The same approach applies to the drSIR $T_1$-filter where the first point is x=$TI_i$/ln 2 with y=−1, and the second point is x=$TI_s$/ln 2 with y=1. $S_{drSIR}$ in the mD is given by:

$$S_{drSIR} \approx \frac{\ln 4}{\Delta TI} T_1 - \frac{\sum TI}{\Delta TI} \quad [21]$$

where □TI=$TI_s - TI_i$ which is negative, and $\tau TI = TI_s$. Since □TI is negative, the slope $$\frac{\ln 4}{\Delta TI}$$

in Eq. [21] is negative (e.g., FIGS. 15A and 15C). The offset is positive.

The expressions in Eqs. [20] and [21] capture four aspects of the dSIR and drSIR $T_1$-filter, firstly, the near linear change in signal with $T_1$ in the mD, secondly, the $T_1$-filters have slopes equal to $$\frac{\ln 4}{\Delta TI},$$

and thirdly, the $T_1$-filter show high contrast sensitivity for small changes in $T_1$ when the size of ΔTI is small $$\left(\text{since } \square S_{dSIR} \approx \frac{\ln 4}{\Delta TI}\square T_1\right.$$

and $$\left.\square S_{drSIR} = \frac{\ln 4}{\Delta TI}\square T_1\right).$$

As □ TI decreases in magnitude, amplification of contrast increases (Table 2). Fourthly, the equations can be used to map $T_1$ in the mD since for $S_{dsIR}$ and $S_{drSIR}$:

$$T_1 \approx \frac{\Delta TI}{\ln 4} S_{dSIR} - \frac{\sum TI}{\ln 4} \quad [22]$$

$$T_1 \approx \frac{\Delta TI}{\ln 4} S_{drSIR} - \frac{\sum TI}{\ln 4} \quad [23]$$

Figure 26:
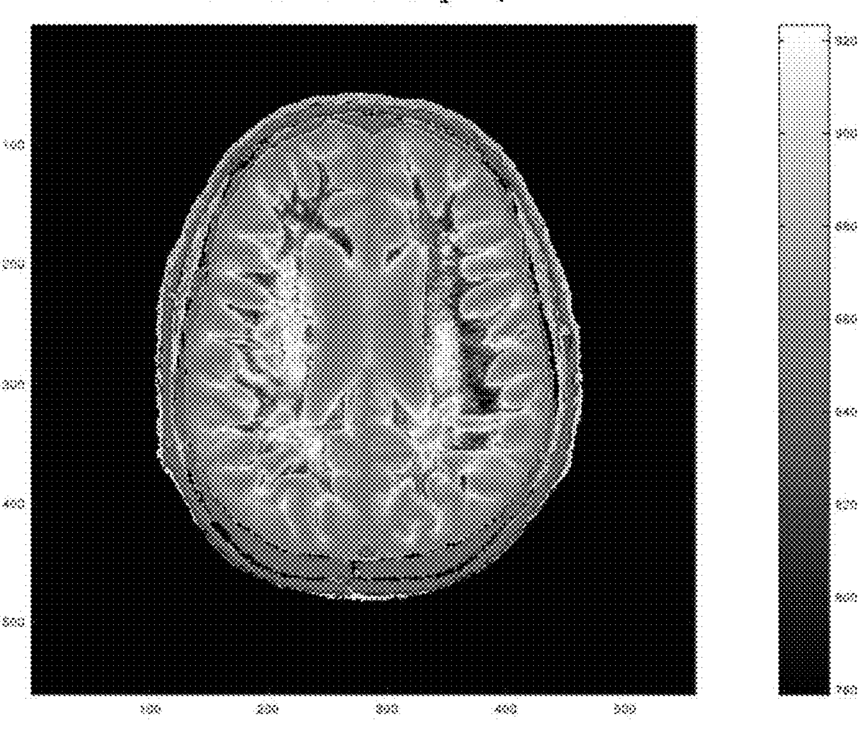
FIG. 26 illustrates narrow mD dSIR image/$T_1$ map in a patient with small vessel disease, according to one example.

The $S_{dSIR}$ and $S_{drSIR}$ maps show high contrast and high spatial resolution (e.g., FIG. 26). The linear approximation is only valid in the mD. Also, it is assumed that TR is long otherwise $T_1$ values may require correction for incomplete recovery of longitudinal magnetization during TR. It is also assumed that the nulling of the baseline tissue is accurate.

FIG. 26 illustrates narrow mD dSIR image/$T_1$ map ($TI_s$=540 ms and $TI_i$=640 ms, □ TI=18%, TR=6000 ms) in a patient with small vessel disease showing $T_1$ values within the mD on the grayscale at the right. The $T_1$ grayscale covers the mD which is within white matter. The grayscale shows $T_1$ values over a range of 144 ms with the dark low signal representing shorter normal $T_1$ values in white matter of 780 ms (i.e. 540/ln 2 ms) and above, and higher signal representing abnormal increased $T_1$ values in white matter up to the maximum of 924 ms (i.e. 640/ln 2 ms).

The full display grayscale ranges from +1 to −1 and linearly covers a 144 ms difference in $T_1$. With conventional $T_1$ maps of the brain and CSF the grayscale range typically covers 2000-4000 ms. Thus, there is much greater display sensitivity to differences in $T_1$ in the mD with the dSIR image than with conventional $T_1$ maps.

Lesions with $T_1$ values greater than the maximum in the mD (i.e., greater than 924 ms) "overshoot" and have a mid-gray centre (where $T_1$ values shown on the grayscale are unreliable) and are surrounded by high signal boundaries.

$T_1$ mapping is only valid in the mD. If TR is short, the values may be low and need correction. In this case, the source images were obtained using a long TR IR sequence.

2.10 Synthetic MASDIR and MASDEA as Well as Synthetic $T_1$-, $T_2$-, $T_2$*- and D*-Bipolar Filter Images (a) Synthetic narrower mD dSIR and drSIR images can be generated from wider mD dSIR and drSIR images. The wider mD images are used to calculate Tis and these can be used in any equation for dSIR or drSIR images which have Tis within the mD of the wider mD images. This can be used to provide many narrower mD images with different nulling Tis and ΔTis without requiring any additional data acquisition. This provides flexibility to observe the effects of changing Tis on image contrast.

Figure 27:
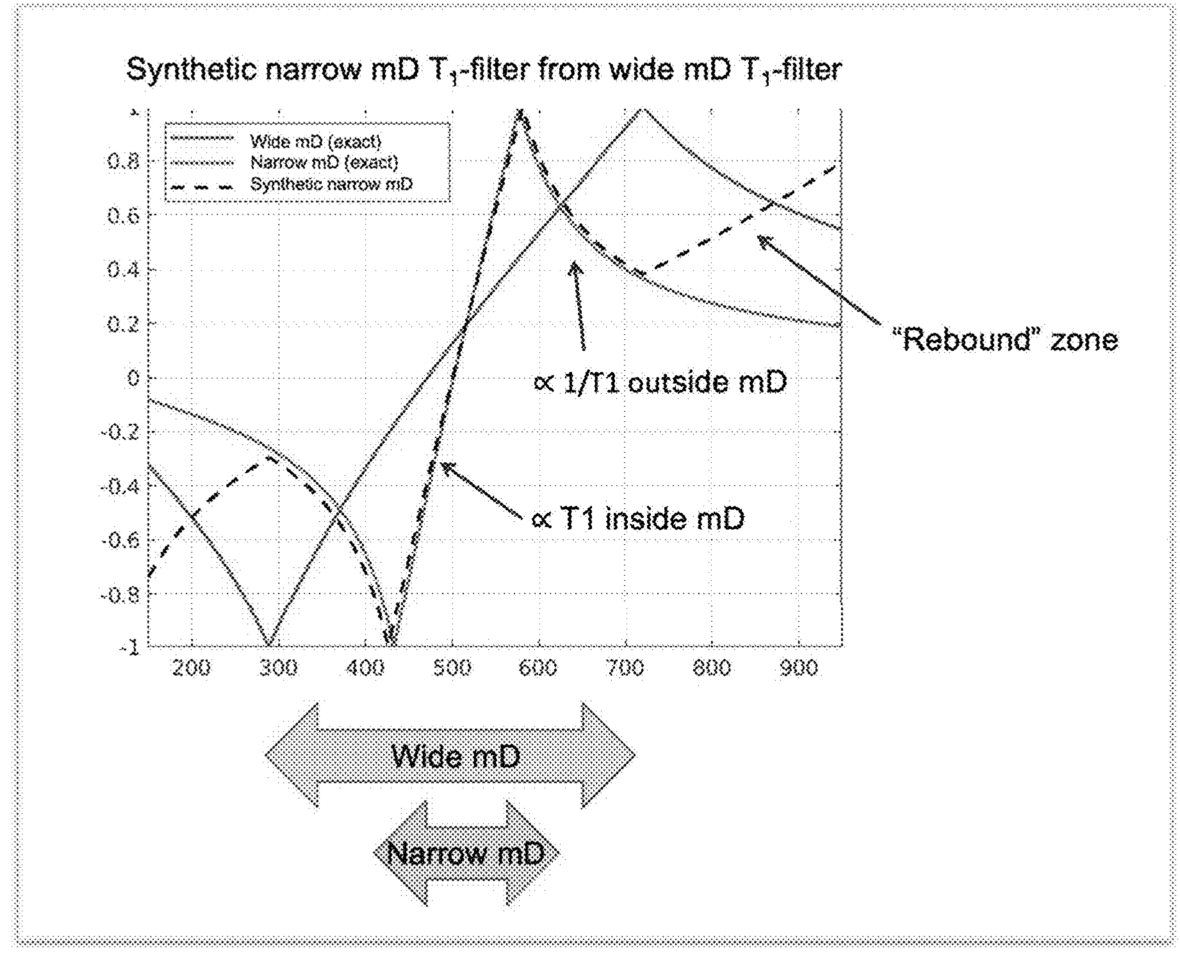
FIG. 27 illustrates a wider mD $T_1$-bipolar filter with a narrow mD $T_1$-bipolar filter and a synthetic narrow mD $T_1$-bipolar filter, according to one example.

FIG. 27 illustrates a wider mD $T_1$-bipolar filter (blue) shown with a narrow mD $T_1$-bipolar filter (yellow) and a synthetic narrow mD $T_1$-bipolar filter (dashed lines) created from the wide mD $T_1$-bipolar filter. The synthetic $T_1$-bipolar filter closely approximates the narrow mD $T_1$-bipolar filter within the wide mD of the wide $T_1$-bipolar filter. It is proportional to $T_1$ in the narrow mD $T_1$-bipolar filter and is proportional to $1/T_1$ outside the narrow mD $T_1$-bipolar filter. It shows a "rebound" zone outside the wide mD.

FIG. 27 shows a wide mD $T_1$-bipolar filter (blue), a narrow mD $T_1$-bipolar filter (yellow) and a synthetic narrow mD $T_1$-filter (dashed lines). The mD of the wide mD $T_1$-bipolar filter is shown with the wide double headed arrow below the figure and the mD of the narrow mD $T_1$-bipolar filter is shown by the narrow double headed arrow below the figure. The synthetic narrow mD $T_1$-bipolar filter closely follows the narrow mD $T_1$-bipolar filter within the wide mD. Outside of this there are "rebound" zones where the synthetic $T_1$-bipolar filter deviates from the narrow mD $T_1$-bipolar filter. The signal from the narrow mD $T_1$-bipolar filter and the synthetic $T_1$-bipolar filter is proportional to $T_1$ in the narrow mD. It is approximated by $1/T_1$ outside the narrow mD, but within the wide mD. This shows that the narrow mD $T_1$-bipolar filter can be accurately approximated by the synthetic narrow mD $T_1$-bipolar filter within the narrow mD.

When complex data are available the "rebound" can be avoided by making use of the phase difference (phi) between the IR images. The value of phi can be either ±π (inside the mD) or 0 (outside the mD). If the absolute value of phi (|phi|) is closer to 0 than to π, then it indicates the dSIR is outside the mD and should be modified. The modification consists of replacing the dSIR value with (−2-dSIR) if dSIR <=0 or with (2-dSIR) if dSIR >0.

One application of the synthetic procedure is to remap the dSIR from one mD to another. One advantage is that the Tis needed to produce a specific image contrast can be generated in post-processing rather than by acquiring data prospectively.

Another application is to use a slightly wider TI spacing to move signal nulls outside the mD since these incur noise bias. The dSIR with the desired nullpoints can then be synthesized.

Figure 28:
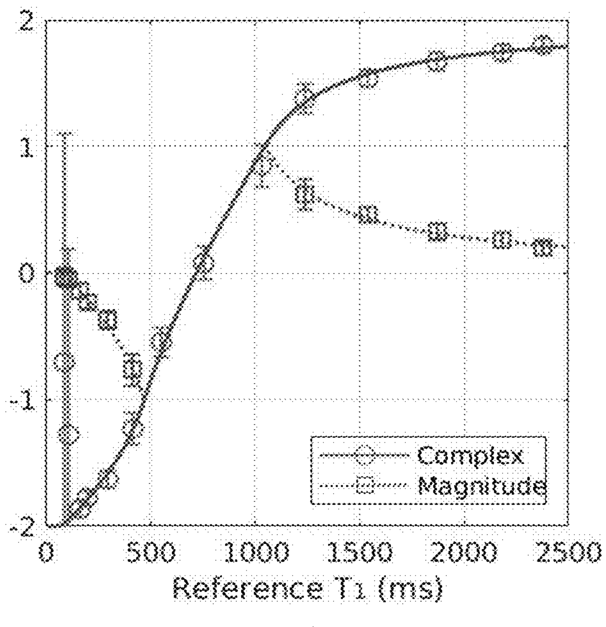
FIG. 28 illustrates a plot having numeric values (+/− standard deviation) of the dSIR in phantoms with known reference $T_1$ values, according to one example.

Validation of the dSIR model is shown in FIG. 28 in which signal values are plotted against known $T_1$ values in standard phantoms for the dSIR sequence in phase corrected and magnitude form. There is close agreement supporting the validity of the dSIR model.

FIG. 28 illustrates a plot having numeric values (+/− standard deviation) of the dSIR in phantoms with known reference $T_1$ values. Square markers (dotted line) represent the regular dSIR generated from magnitude images and the circle markers (solid line) represent the modified form using the phase difference of complex images.

(b) dSIR and drSIR images are only dependent on $T_1$ and they can be synthesized from $T_1$ maps acquired using MP2RAGE (3), shMOLLI (6), UTE-AFI-STR (7), magnetic resonance fingerprinting (8) and other techniques.

(c) Synthetic $T_2$-, $T_2$*- and D*-Bipolar Filters.

In one example, the concepts underlying the $T_1$-bipolar filters are extended to use $T_2$, $T_2$* and D* maps to create synthetic $T_2$-, $T_2$*- and D*-bipolar filters. These have linear mDs and reciprocal functions (a/TP) in their lowest and highest Domains (i.e. along their X axes) as illustrated in FIG. 27 for $T_1$, but for $T_2$, $T_2$* and D*. $T_2$-, $T_2$*- and D*-bipolar images can be synthesized with positive (p) or negative (n) slopes. The widths of their mDs are defined by differences in sequence parameters, □SP, which have the forms □TE, □TE and □b for the $T_2$-, $T_2$*- and D*-bipolar sequence images, respectively. □

(d) Combinations of $T_1$-, $T_2$-, $T_2$*- and D*-Bipolar Filters.

Two or more synthetic $T_1$, $T_2$-, $T_2$*- and D*-bipolar filters can be multiplied together to produce synergistic contrast. The $T_1$, $T_2$-, $T_2$*- and D*-bipolar filters can have positive (p) or negative (n) slopes so that for either sign of the change in $T_2$, $T_2$* or D* (positive or negative) the image contrasts for each TP can all be made positive, or all be made negative to provide overall synergistic positive or negative image contrast.

(e) Phase Mapping with Tissue Property Bipolar Filters.

Bipolar filters may also be applied to phase maps of susceptibility, chemical shift, velocity and other tissue properties. These can be used to selectively highlight areas with small changes without producing saturation of voxels, coalescence of voxels and loss of anatomical detail as with conventional narrow windowing of images.

(f) Normal Appearing Tissues

Synthetic $T_1$-, $T_2$-, $T_2$*- and D*-bipolar filter images are of particular value in targeting small changes in TPs in normal appearing tissues. The small changes in TPs may be insufficient to produce useful contrast with conventional pulse sequences. One example of the present subject matter can be configured to reveal abnormalities in normal appearing tissues such as white and gray matter of the brain.

2.11 Log Subtracted Inversion Recovery (lSIR)

Given magnitude images ($M_1$ and $M_2$) acquired at two different Tis, the dSIR image is calculated from the following equation.

$$dSIR=(M_1-M_2)/(M_1+M_2) \quad [24]$$

As the difference in TI becomes smaller the formula becomes a differential $$dSIR \to dM/2M = d\ln(M) \quad [25]$$

which suggests a modified form of dSIR calculated by subtracting the log images. This is referred to as log subtracted inversion recovery (lSIR).

$$lSIR = 1/2\ln(M_1) - 1/2\ln(M_2) \quad [26]$$

Figure 29:
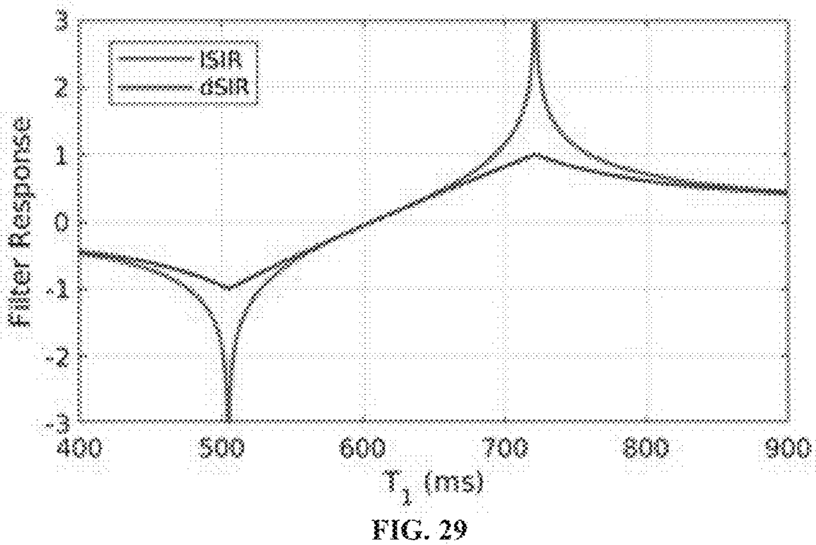
FIG. 29 illustrates a filter response, according to one example.

The lSIR is related to dSIR by the inverse hyperbolic tangent lSIR=atanh(dSIR) and its $T_1$ filter response is given in FIG. 29.

FIG. 29 illustrates response of the lSIR (red) and dSIR (blue) filters to $T_1$. The bipolar shape is amplified in the vicinity of the nullpoints. In this example the nullpoints were chosen to be 505 ms and 721 ms corresponding to Tis of 350 ms and 500 ms.

Based on an understanding of contrast as slope versus $T_1$ it is clear that the lSIR image has increased contrast at the nullpoints as compared to the dSIR image. When the higher nullpoint is intermediate between two tissues with distinct $T_1$s—such as white and gray matter—the ability to resolve features at the tissue interface is increased.

This is because fast exchange of the magnetization between white and gray matter causes the observed $T_1$ at the interface to be a weighted average of the individual tissue T1s governed by the volume fraction ($\eta$). As $\eta$transitions from 0 to 1 (white to gray matter) the $T_1$ takes on every value between $T_1$(white) and $T_1$(gray) including the extremely sharp response at a particular value of $\eta$.

The lSIR arises from considering the difference log images but in principle other custom-designed filters, e.g. dSIR/(1−½dSIR$^4$), could produce a similar result. If complex images are used in Eq 26 instead of magnitude, the real part contains the filtered $T_1$ and the imaginary part contains the phase difference between the IR images. Filters (lSIR, dSIR, MP2RAGE, FLAWS-hc) may also be applied to $T_1$ maps obtained using other techniques although different results may be observed if the $TI_s$ differ substantially or if a non-IR method of $T_1$ estimation is used.

Figure 30:
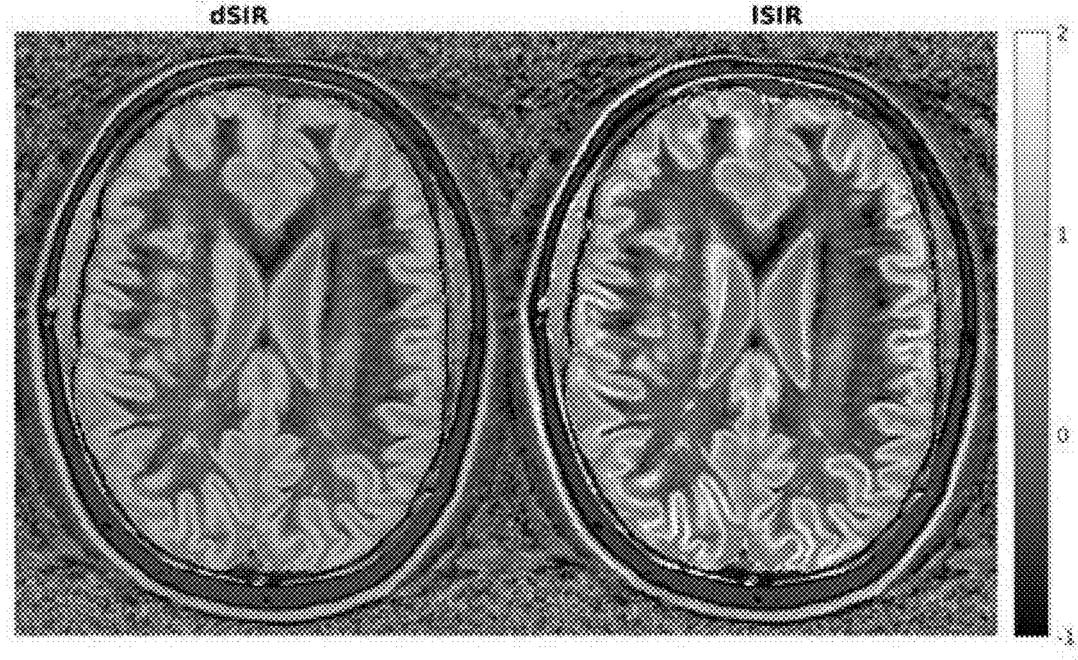
FIG. 30 illustrates a comparison of dSIR and lSIR images, according to one example.

FIG. 30 illustrates a comparison of dSIR and lSIR images in a normal volunteer. The white matter appears black providing a background against which structures with slightly longer Tis appear mid-gray. At the boundary between white and gray matter the intensity reaches a maximum. This is at a $T_1$ intermediate between those of white and gray matter. The top of the colorbar scale is set to +2 to provide additional grayscale range for the lSIR image. Better defined and sharper boundaries are seen on the lSIR images.

Figure 31:
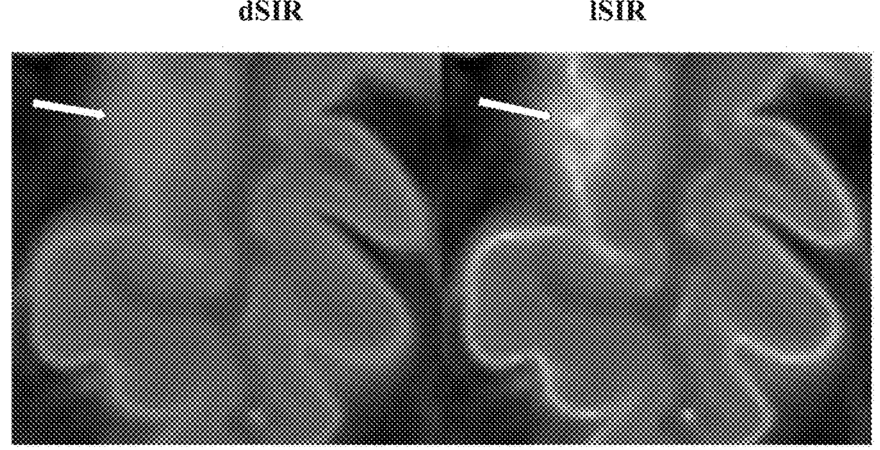
FIG. 31 illustrates morphology at tissue boundaries, according to one example.

FIG. 31 illustrates the increased ability to clarify the morphology at tissue boundaries. Close inspection of the dSIR image (left) reveals the same structures are present but hidden within a grayscale of similar Tis (arrows). The lSIR image (right) provides high contrast across the white matter-gray matter boundary. Boundaries are better seen on the lSIR image where structure is seen in the abnormal region that appears blurred on the dSIR image (arrows).

2.12 Ultra-High Contrast MRI (UHC MRI)

Synthetic TP-bipolar filter images can produce an order of magnitude increase in contrast compared with conventional IR sequences. This allows previously invisible changes in relaxation times to be manifest as visible changes in contrast with TP-bipolar filter sequences.

A similar order of magnitude increase in contrast can be produced by changing opposed $T_2$ and diffusion contrast to synergistic $T_1$ and $T_2$ as well as $T_2$ and diffusion contrast.

2.13 Examples

Figures 32A, 32B:
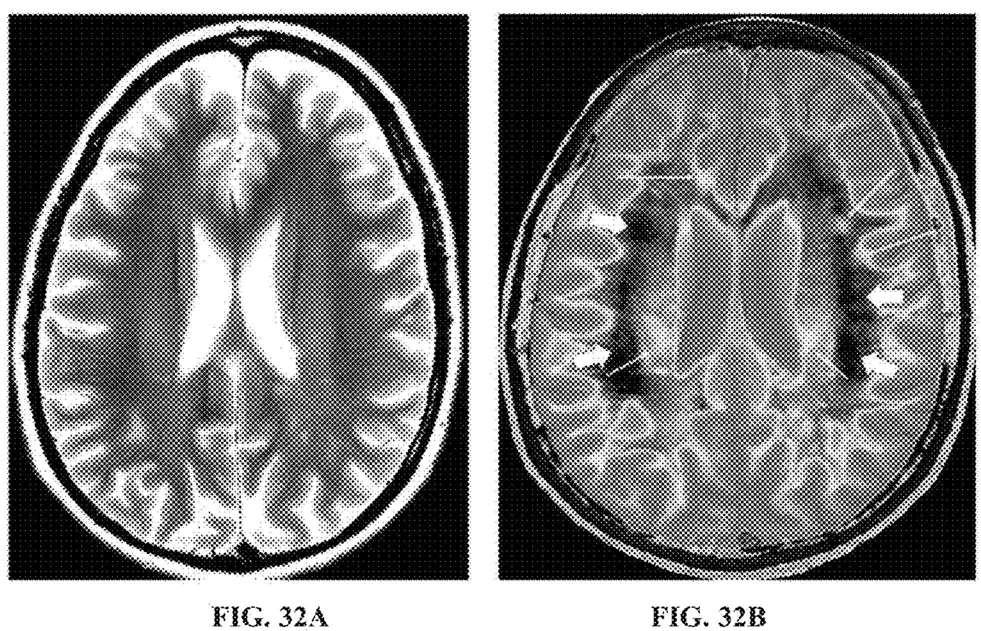
FIGS. 32A and 32B illustrate a comparison of a $T_2$-wSE image with a narrow mD dSIR image, according to one example.

Application can be seen in a case of Multiple Sclerosis (MS) (FIGS. 32A and 32B) which compares a $T_2$-wSE image (FIG. 32A) with a narrow mD dSIR image (FIG. 32B).

FIGS. 32A and 32B illustrate a case of MS. Comparison of 2D $T_2$-wSE (FIG. 32A) and narrow mD dSIR (FIG. 32B) images using similar spatial resolutions and slice thicknesses. The narrow mD dSIR sequence is targeted to null normal white matter and produce high positive contrast from small increases in $T_1$ from the normal $T_1$ of white matter. No abnormality is seen on the $T_2$-wSE image, but three focal lesions are seen on the dSIR image (long thin arrows). The corticospinal tracts are also abnormal (short thin arrows). The normal superior longitudinal fasciculi are of intermediate signal in FIG. 32B. More peripheral white matter appears dark and much of it is normal in FIG. 32B (thick arrows). Thus, the lateral peripheral normal appearing white matter in FIG. 32A is mostly normal in FIG. 32B. A high signal boundary is seen between white matter and cortical gray matter as well as at the white matter-CSF boundary around the lateral ventricles.

The image of FIG. 32B is targeted at null normal white matter and produces high positive contrast from small increases in $T_1$ from normal in white matter. No abnormality is seen in FIG. 32A but three focal lesions are seen in FIG. 32B (long thin arrows). One is in white matter, another is at the junction between white and gray matter (anterior) and the other is at the junction between white and gray matter but mostly in gray matter (left). Localization of lesions is helped by the well-defined high signal white matter gray matter boundaries. Normal white matter seen laterally has a low signal (dark) appearance in FIG. 32 B (thick arrows). Intermediate signal is seen in the more medial normal superior longitudinal fasciculi in FIG. 32B.

Figures 33A, 33B:
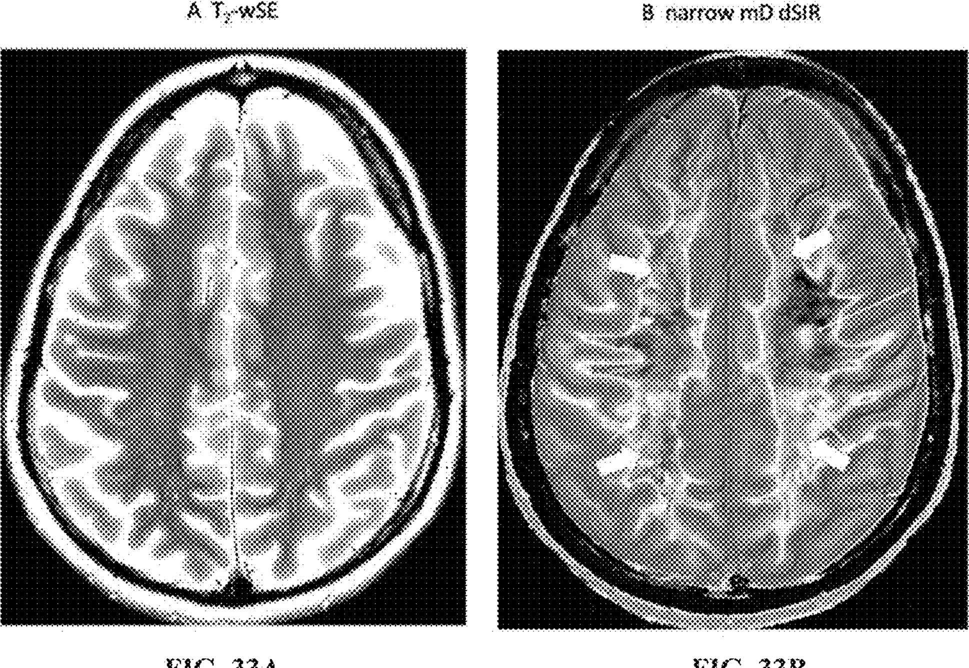
FIGS. 33A and 33B illustrate a higher slice, according to one example.

FIGS. 33A and 33B illustrate a higher slice in the same case as in FIGS. 32A and 32B where a $T_2$-wSE image is compared with a narrow mD dSIR image.

FIGS. 33A and 33B illustrate the same case of MS as in FIG. 32 shown at a higher level. Comparison of $T_2$-wSE (FIG. 33A) and narrow mD dSIR (FIG. 33B) images. The narrow mD dSIR sequence is targeted to null normal white matter and produce high positive contrast from small increases in $T_1$ from the normal $T_1$ in white matter. A focal lesion that is not seen on the $T_2$-wSE is seen on the dSIR image (long thin arrow) and other abnormalities are seen in the corticospinal tracts (short thin arrows). The white matter appears normal on the $T_2$-wSE image FIG. 33A but most of it has a high signal and appears abnormal on the narrow mD dSIR image FIG. 33B (thick arrows). Only about 5-10% of the white matter in FIG. 33B has a normal dark appearance. The normal appearing white matter in FIG. 33A mostly appears abnormal in FIG. 33B. High signal boundaries are seen between white matter and cortical gray matter.

No abnormality is seen on the $T_2$-wSE image FIG. 33A but a focal lesion is seen on the dSIR image (long thin arrow) FIG. 33B. The corticospinal tracts are also seen (short thin arrows). There are areas of increased signal in most of the white matter in FIG. 33B (thick arrows). Only about 5-10% of the white matter in this figure has a low signal (dark) and appears normal. High signal, high contrast boundaries are seen between white and gray matter.

In FIG. 32A most of the normal appearing white matter on the $T_2$-wSE image shows as normal tissue with a dark (low) signal appearance in (FIG. 32B) (thick arrows). In FIG. 33 most of the normal appearing white matter in (FIG. 33A) shows as abnormal high signal (light) in (FIG. 33B) (thick arrows).

Figure 34:
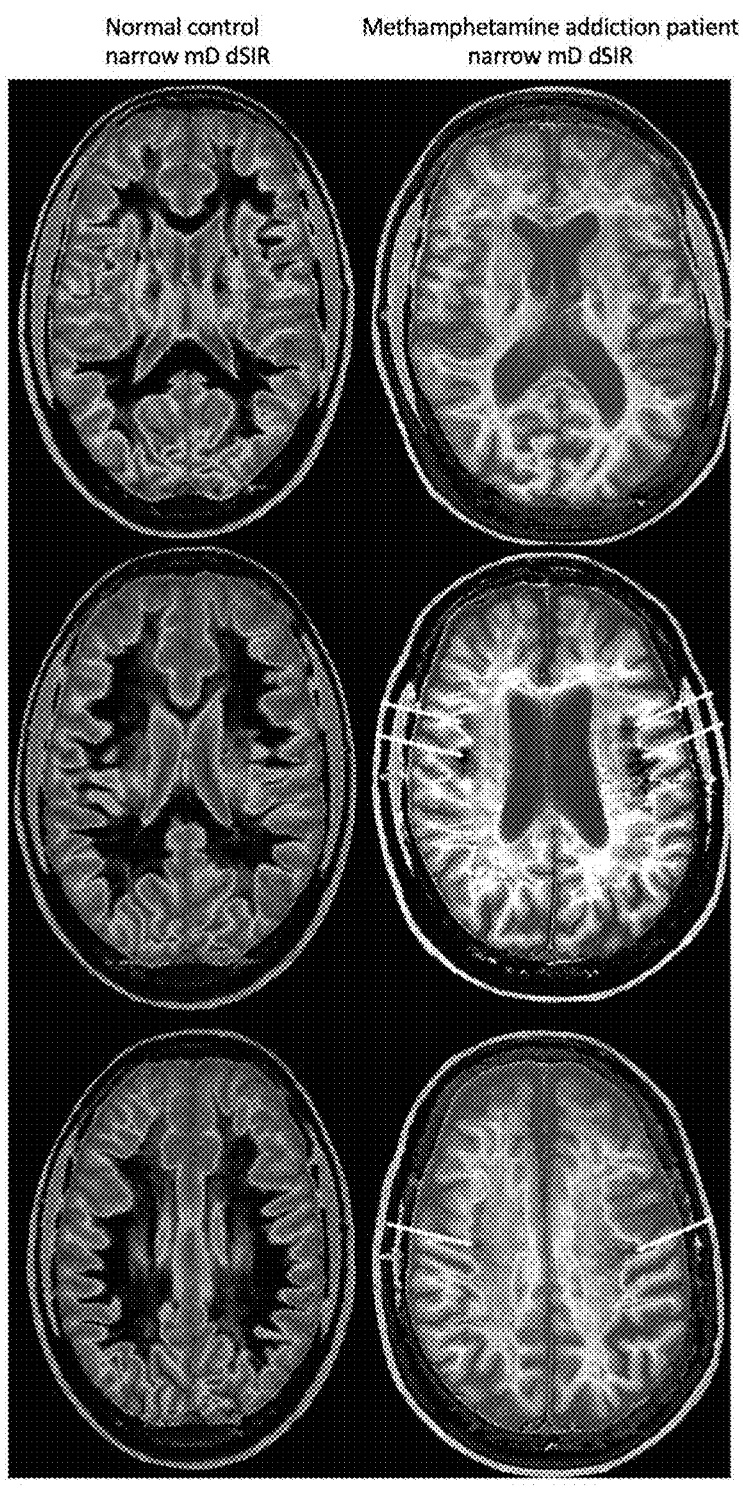
FIG. 34 illustrates a comparison of images, according to one example.

FIG. 34 shows narrow mD dSIR images in a normal age, gender, ethnicity and socio-economically matched control (left column), and a 49-year-old patient with methamphetamine addiction for 20 years followed by an abstinence period of 120 days (right column).

FIG. 34 shows 2D narrow mD dSIR images in the age, gender, ethnicity, and socioeconomic status matched normal control (left column) and in a 49-year-old male with a 20 year history of methamphetamine use, abstinence period 120 days (right column). The narrow mD sequences are targeted to null normal white matter and highlight contrast produced by small increases in the $T_1$ of normal white matter. The narrow mD dSIR images in the control show normal white matter as low signal (dark). The dSIR images in the methamphetamine patient (right column) show widespread high signal (light) in white matter with only small areas of normal dark white matter (long thin arrows). This is the whiteout sign. Normal high signal boundaries are seen between white matter and gray matter in both sets of dSIR images but are more obvious in the normal control. They are partly obscured by the abnormal high signal in white matter in the patient. Contrast is seen between some normal central white matter in superior longitudinal fasciculi (light) in the normal control and more peripheral normal white matter (dark) (left column).

In the control images, most white matter appears normal with a low signal (dark) (left column), but in the patient most white matter appears abnormal with a high signal (light) (right column). This is the whiteout sign. There is only a small amount of normal white matter (dark) present on the patient's images (thin white arrows, right column).

In the normal control, there is contrast between more peripheral normal white matter (dark) (left column) and more central normal white matter of the superior longitudinal fasciculi (mid-gray).

FIGS. 35A and 35B compare a $T_2$-FLAIR image (FIG. 35A) with a narrow mD dSIR image (FIG. 35B) in the 49-year-old patient described previously.

FIGS. 35A and 35B illustrate images of a methamphetamine addiction patient. Comparison of 2D $T_2$-FLAIR (FIG. 35A) and narrow mD dSIR (FIG. 35B) images with similar spatial resolutions and slice thicknesses in the 49-year-old patient with a 20 year history of methamphetamine use whose images are shown in FIG. 35. There is normal appearing white matter on the $T_2$-FLAIR image (FIG. 35A) but on the narrow mD dSIR image (FIG. 35B) there are extensive areas of higher signal in about 90% of the white matter of the centrum semiovale. This is the whiteout sign. Only small areas of more normal lower signal are seen in this white matter (long thin arrows) FIG. 35B. Thus, most of the normal appearing white matter in FIG. 35A appears abnormal in FIG. 35B. High signal boundaries are seen between white matter and gray matter on the narrow mD dSIR image FIG. 35B.

No abnormality is seen on the $T_2$-FLAIR image (i.e., it shows normal appearing white matter) but extensive high signal abnormalities are seen in white matter on the narrow mD dSIR image. There are only small areas of normal low signal (dark) white matter on this image (thin arrows). It shows the whiteout sign.

Figure 36:
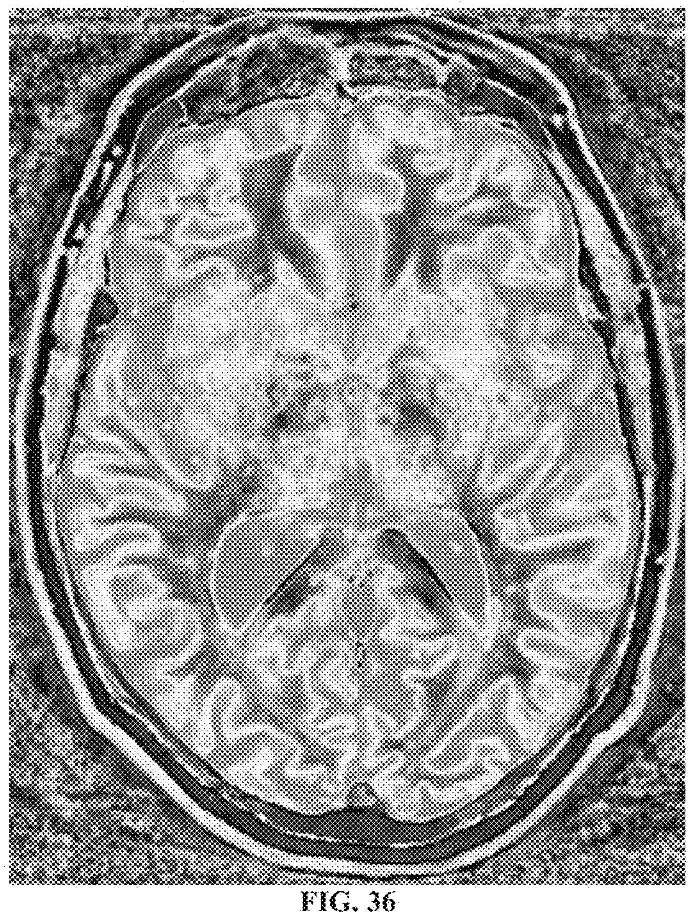
FIG. 36 illustrates an image in a 76 year old patient with Parkinson's Disease, according to one example.

FIG. 36 shows a case of Parkinson's Disease in a patient aged 76 years examined with a dSIR sequence (TIs 350 ms and 500 ms). The high contrast bilaminar cortex sign is seen at the periphery of the hemispheres with high signal in the outer part of the cortex. Numerous small circles are seen in the thalamus and basal ganglia (the bubble sign).

Figures 37A, 37B:
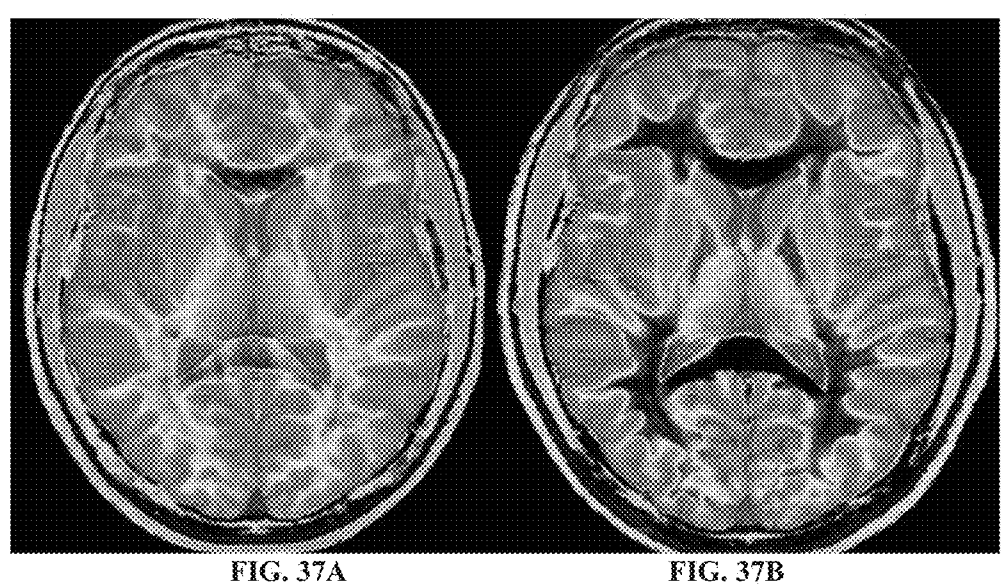
FIGS. 37A and 37B illustrate a case of mild traumatic brain injury, according to one example.

FIGS. 37A and 37B illustrate a case of mild traumatic brain injury (mTBI) in an 18 year old male shown 21 hours after injury FIG. 37A when the patient was symptomatic, and 64 hours after injury FIG. 37B when the patient was asymptomatic. FIG. 37A shows a whiteout sign with high signal (light) in the cerebral hemisphere white matter and the posterior limb of the internal capsule (PLIC). In addition, there is relatively low contrast across the medial and lateral aspects of the thalamus (arrows on the lateral aspects of the thalami). FIG. 37B shows resolution of the whiteout sign with low signal (dark) now apparent in the cerebral hemisphere white matter and the PLIC.

In addition, high signal is now seen in the lateral thalamus and there is high contrast across the thalamus (arrows on the lateral aspects of the thalami). This is a normal appearance of the thalamus. 21 hours after injury the patient had lost gray matter contrast (the grayout sign) FIG. 37A and 64 hours after injury the normal high contrast appearance of the thalamus was seen FIG. 37B with resolution of the grayout sign.

FIGS. 37A and 37B illustrate mTBI in an 18 year old male 21 hours after injury (FIG. 37A) and 64 hours after injury (FIG. 37B). In FIG. 37A, there is a whiteout sign with high signal in the white matter of the cerebral hemispheres including the PLICs. There is low contrast across the thalamus from medial to lateral (arrows on the lateral aspects of the thalami). This is the grayout sign.

On the follow up image at 64 hours the whiteout sign has resolved and white matter including the PLICs appears dark. The thalamus now shows a normal appearance with high contrast from medial to lateral (arrows on the lateral aspects of the thalami). This is resolution of the grayout sign shown in FIG. 37A back to normal FIG. 37B.

3. Selected Aspects (Items 3.01-3.18)

3.01 Small Changes in TPs that do not Produce Diagnostic Contrast with Conventional Sequences In some cases, a small change in TP, for example in early stages in disease, or with long standing neuroinflammation of the brain, is insufficient to produce contrast with conventional imaging sequences. As a result, the images show normal appearing tissues such as white or gray matter in the brain, and the patient's disease is not recognized. dSIR and drSIR sequences can provide 5-15 times the contrast of conventional sequences for small changes in $T_1$ in disease, and the sequences frequently show subtle abnormalities with high contrast and thus allow diagnosis of occult disease of the brain not seen with conventional sequences.

3.02 Opposed Contrast from Two Different TPs Resulting in Low Net Contrast and Non-Diagnostic Images In some examples, contrast produced by an increase in a selected TP, such as $T_2$, is opposite in sign to the contrast produced by concurrent increase in another TP, such as D* (apparent diffusion coefficient). The contrast produced by the increases in $T_2$ and D* cancels out and the resulting images show low contrast despite a relatively large change in the two TPs.

According to one example of the present subject matter, images are produced that reverse the sign of the contrast produced by one or more of the TPs to make the overall net contrast synergistic for the two TPs, and therefore more visible and recognizable.

3.03 Quantitation

Quantitation of $T_1$ usually requires an additional acquisition. dSIR and drSIR images are related to $T_1$ maps and these are accurate in the mD making high quality $T_1$ mapping an intrinsic part of clinical imaging.

3.04 Boundaries between tissues and around lesions may be difficult to discern and can be shown with high contrast using TP-bipolar filter sequences.

3.05 Effects due to shortening of $T_1$ due to GBCAs may be subtle or not apparent with conventional sequences, but the contrast produced by the shortening of $T_1$ can be increased 5-15 times compared with conventional $T_1$-weighted IR sequences and made visible.

3.06 Demonstration of Small Changes in $T_1$, $T_2$, $T_2$* and D*

One example of the present subject matter includes synthetic dSIR and drSIR images. dSIR and drSIR images can be seen as complementary to other sequences such as Magnetization Prepared—RApid Gradient Echo (MP-RAGE), $T_2$-weighted Spin Echo ($T_2$-wSE) and $T_2$-FLuid Attenuated Inversion Recovery ($T_2$-FLAIR). According to one example, synthetic dSIR and drSIR images can reveal brain disease.

3.07 Making Opposed Contrast into Synergistic Contrast

Synergistic contrast can show abnormalities with high contrast in chronic diseases of the brain where there is a concurrent increase in $T_2$ and D* resulting in little or no useful contrast.

3.08 Quantitation

One example of the present subject matter allows for quantitation as a part of an examination. Quantitation can facilitate objective measurement for monitoring disease progression and response to therapy.

3.09 Education

Examples of the present subject matter can help explain contrast using, for example, TP-bipolar filters. These examples can explain targeting, image, signal, contrast, weighting, boundaries, quantitation and the effects of GBCA enhancement.

3.10 MP2RAGE (Magnetization Prepared 2 RApid Gradient Echo)/FLAWS-uni employ multiplication addition and division (but not subtraction) of IR images. MP2RAGE shows a relatively small increase in $T_1$ contrast over a broad domain of $T_1$ values. The MP2RAGE sequences use two widely spaced fixed inversion times ($TI_s$). They are not targeted at a single tissue or small changes in the $T_1$ of that tissue in disease and do not show very high contrast amplification. They do not have $T_1$-bipolar filters.

On the other hand, directly acquired and synthetic dSIR and drSIR $T_1$-bipolar filters show very high contrast for small changes in $T_1$ over a narrow domain. They are $T_1$-bipolar filters.

3.11 FLAWS-hc (FLuid And White matter Suppression high contrast) and FLAWS-hco (FLuid And White matter Suppression high contrast opposite) are similar to MP2RAGE/FLAWS-uni in that the sequences use widely spaced fixed TIs which are not targeted at small changes in $T_1$ in a single tissue. They do not achieve high contrast in a narrow mD and do not utilize $T_1$-, $T_2$-, $T_2$*- or D*-bipolar filters (see FIG. 1, Beaumont J et al. Magn Reson Med 2021; 85(3):1364-1378 in Selected Publications (5)).

3.12 Synergistic contrast between $T_2$ and D* may occur by happenstance when $T_2$ is increased and D* is increased in disease, as exploited by Diffusion Weighted Imaging with Body Signal Suppression (DWIBS). By reversing $T_2$ and/or D* contrast, it is possible to make $T_2$ and D* contrast synergistic for any combination of changes in sign of the two properties, and so change opposed contrast into synergistic contrast.

3.13 Multiple Sclerosis (FIGS. 32A, 32B and 33A, 33B)

In FIG. 32A no abnormality is seen with $T_2$-wSE image (A) but extensive changes are seen in on the dSIR image (B). In FIG. 33A, no abnormality is seen with $T_2$-wSE images (A) but a focal lesion and extensive diffuse changes are seen on the dSIR image (B).

3.14 Methamphetamine Addiction (FIGS. 34 and 35)

In FIG. 34 (left column) (normal control) the normal white matter is black, but in FIG. 34 (right column) (patient with methamphetamine addiction) extensive abnormal white areas are seen in the white matter and only small areas of dark normal white matter seen (arrows). FIG. 35 compares the $T_2$-FLAIR image at the higher level (A) with the dSIR image (B). No abnormality is seen in the conventional image (A) but very extensive abnormalities are seen in (B).

3.15 The FLAWS (Fluid and White Matter Suppressed) sequence was originally described with $TI_s$ chosen to null the signal from fluid and from white matter and these were combined by multiplication and normalized. It was related to the MP2RAGE sequence which also multiplies and normalizes two IR sequences using the sum of the squares of the sequence signals in the denominator. The FLAWS sequence has been extended to include subtraction and normalization in the form of FLAWS-hc (FLAWS high contrast) and FLAWS-hco (FLAWS high contrast opposed) sequences which employ subtraction. It differs from dSIR and drSIR sequences because two fixed widely spaced values of TI are used rather than TI selected to target small changes in $T_1$ in disease in a specific tissue.

An example of the present subject matter can be configured to target a small change in TP. FLAWS and FLAWS-uni/MP2RAGE, on the other hand, do not show high contrast regions and do not show high signal boundaries with high contrast. One example of the present subject matter includes narrow mD TP-bipolar filters and exhibits high signal boundaries.

The FLAWS-hc and FLAWS-hco sequences with TIs of 620 ms and 1430 ms have essentially monotonic $T_1$-filters without a steeply sloping mD. They provide generally increased contrast over wide $T_1$ domains but not the very high contrast seen with narrow mD dSIR and drSIR sequences. They do not use magnitude reconstruction and their $T_1$-filters are essentially monotonic, not bipolar.

The FLAWS-uni sequence (MP2RAGE) with TIs of 800 ms and 2700 ms has a lower magnitude of its slope than FLAWS-hc and FLAWS-hco. It is also essentially flat for small increases in $T_1$ in gray matter (5).

None of the FLAWS-hc, FLAWS-hco or FLAWS-uni/MP2RAGE sequences show the sharply defined $T_1$-bipolar filters seen with narrow mD dSIR and drSIR sequences or their synthetic bipolar forms produced from wider dSIR and drSIR sequences or from $T_1$, $T_2$, $T_2$*and/or D* maps. They do not produce high contrast for small changes in TPs as narrow mD TP-bipolar filters do, nor do they produce high signal sharply defined boundaries.

3.16 High Contrast Synthetic Images

This can be created in four ways: (a) from wider dSIR and drSIR images to produce narrower dSIR and drSIR $T_1$-bipolar filter maps. (b) from $T_1$ maps to produce $T_1$-bipolar filter images. (c) from $T_2$, $T_2$* and/or D* maps to produce $T_2$-, $T_2$*- and/or D*-bipolar filter images. (d) from combinations of $T_1$-, $T_2$-, $T_2$*- and D*-bipolar filter images to produce synergistic contrast multi TP images.

With conventional images, narrowing of window width increases contrast but signal values at the top and bottom of the range of narrowly windowed images are saturated so a significant number of voxels in the image have the same high or low signal values. This results in coalescence of the voxels and loss of anatomical detail. It provides a practical limit on how much images can be narrowed before they lose credibility.

With dSIR and drSIR images and other TP-bipolar filter images contrast is amplified but signal values do not become saturated at upper and lower signal boundaries. Values are reflected across the high and low signal boundaries and there is enough slope in the bipolar filters to preserve basic anatomical structures. High contrast images therefore look coherent, unlike very narrowly windowed conventional images or TP maps.

3.17 Further Information

See documents 1-2.

3.18 the Basic MR System

Figure 38:
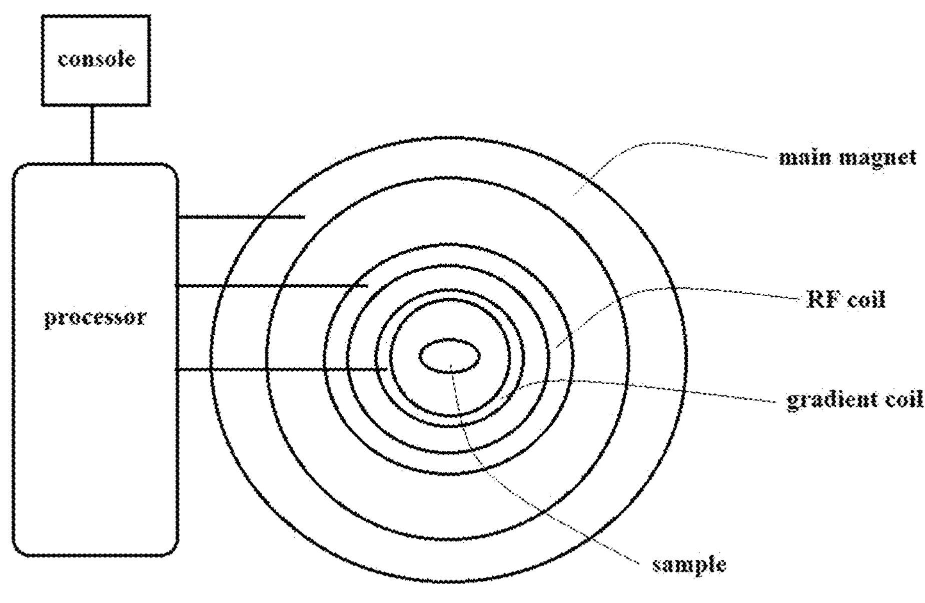
FIG. 38 includes a schematic diagram of a system, according to one example.

FIG. 38 includes a schematic diagram of a system configured to implement examples of the present subject matter. The system includes main magnet, RF coil, and gradient coil, each of which are coupled to a processor. The processor is coupled to a user interface, here denoted as a console. A sample within the field of the main magnet can be imaged using a system configured to implement a pulse sequence and imaging procedure as described herein. For example, the processor can include a digital processor, amplifiers, drivers, and other components to cause the system to execute a MASDIR, MASDEA and other imaging procedures.

4. Various Notes

The following selected examples are practical applications of the disclosed subject matter:

Example 1: MASDIR Sequences

A method for generating ultra-high contrast bipolar filter (BLAIR) magnetic resonance images using Multiplied, Added, Subtracted and/or Divided Inversion Recovery (MASDIR) sequences, including:

a) acquiring two inversion recovery images with different inversion times;

b) performing mathematical operations (multiplication, addition, subtraction, and/or division) on these images; and c) generating an image data set based on these operations.

The method encompasses divided subtracted inversion recovery (dSIR), divided reverse subtracted inversion recovery (drSIR), and logarithmic subtracted inversion recovery (lSIR) techniques.

Example 2: MASDEA Sequences

A method for generating ultra-high contrast bipolar filter (BLAIR) magnetic resonance images using Multiplied, Added, Subtracted and/or Divided Echo Acquisition (MASDEA) sequences, including:

a) acquiring two echo acquisition signals;

b) performing mathematical operations (multiplication, addition, subtraction, and/or division) on these signals;

c) generating an image data set based on these operations; and d) creating synthetic 2D and 3D MR images with ultra-high contrast of normal and abnormal human anatomy.

Example 3: Synthetic MASDIR and MASDEA Images

Techniques for creating synthetic ultra-high contrast bipolar filter (BLAIR) 2D and 3D MR images:

a) synthesizing narrower middle domain (mD) dSIR and drSIR $T_1$-bipolar filter images from wider mD MASDIR sequences;

b) creating synthetic dSIR and drSIR images from $T_1$ maps using $T_1$-bipolar filters;

c) generating synthetic $T_2$-, $T_2$*-, and D*-bipolar filter images from their respective maps;

d) combining directly acquired and synthetic bipolar filter images to achieve synergistic contrast using multiple tissue properties ($T_1$, $T_2$, $T_2$*, and/or D*); and e) utilizing phase differences to create synthetic dSIR images.

Example 4: Resolution of Window Width and Level Display Problems

Use of Tissue Property bipolar filters to create high-contrast images from Tissue Property maps without signal saturation at upper and lower levels, avoiding the limitations of conventional narrow windowing techniques that can result in loss of anatomical detail.

Example 5: High and Low Signal Tissue and Fluid Boundaries

Production of sharply defined high and low signal boundaries between tissues (e.g., white and gray matter) and fluids using dSIR and drSIR sequences, aiding in anatomical determination, abnormality localization, and definition of lesion extent.

Example 6: $T_1$ Measurement Using dSIR and drSIR Images

Quantitative $T_1$ determination within the middle Domain (mD) of dSIR and drSIR images using linear approximation, and in the lowest and highest domains using signal equations.

Example 7: Contrast Enhancement with Gadolinium-Based Contrast Agents (GBCAs)

Use of targeted bipolar filter, drSIR and drSIR sequences before and after GBCA administration to show amplified signal increases (contrast enhancement) in normal tissues and lesions.

Example 8: Contrast Enhancement with Magnetic Iron Oxide Particles (MIOPs)

Utilization of MIOPs with $T_2$*-sensitized dSIR and drSIR sequences to produce synergistic positive contrast through $T_1$ reduction (amplified by drSIR) and $T_2$* reduction.

Example 9: Serial Studies for Small Change Detection

Use of 2D and 3D dSIR, drSIR, and other TP-bipolar filter images in registered serial studies to detect subtle changes in normal anatomy and abnormal tissues, valuable for monitoring contrast enhancement and disease progression or treatment response.

Example 10: Magnetization Transfer (MT) with TP-Bipolar Filter Sequences

Incorporation of incidental or intentional MT effects in dSIR, drSIR, and other TP-bipolar filter acquisitions, manifesting as reductions in observed mobile proton density and $T_1$, with potential for increased sensitivity to tissue abnormalities.

Example 11: Synergistic $T_2$ and D* Contrast

Use of reversed $T_2$ and D* filters to create synergistic contrast from increases or decreases in $T_2$ and D*, enhancing lesion visualization in pulsed gradient spin echo, dSIR, and drSIR sequences.

Example 12: Perfusion-Sensitive Imaging

Use of slice-selected and non-slice-selected inversion pulses with dSIR and drSIR sequences to demonstrate and quantify tissue perfusion through manipulation of blood longitudinal magnetization.

Example 13: Functional MRI (fMRI) with $T_1$ and $T_2$*-Bipolar Filter Sequences Combination of perfusion-sensitive dSIR and drSIR sequences with $T_2$*-weighted acquisitions to detect changes in perfusion and blood susceptibility during brain activation.

Example 14: Molecular Oxygen Effect Imaging

Application of $T_1$-sensitive drSIR and dSIR sequences to detect and quantify $T_1$ changes in fluids and tissues related to physiological or pathological oxygen effects, including those induced by high concentration $O_2$ inhalation.

Example 15: Contrast and Non-Contrast Angiography

Use of dSIR and drSIR sequences for angiography including:

a) using $T_1$ decreases in blood due to GBCAs or MIOPs; and b) non-contrast angiography using selective and non-selective inversion pulses to visualize blood flow based on $T_1$ changes.

The description herein includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure.

This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

6. Selected Publications, Each of which is Hereby Incorporated by Reference Herein in its Entirety 1. Ma Y J, Moazamian D, Cornfeld D M, Condron P, Holdsworth S J, Bydder M, et al. Improving the understanding and performance of clinical MRI using tissue property filters and the central contrast theorem, MASDIR pulse sequences and synergistic contrast MRI. Quant Imaging Med Surg. 2022; 12(9):4658-4690.
2. Ma Y J, Moazamian D, Port J D, Edjlali M, Pruvo J-P, Hacein-Bey L, et al. Targeted MRI (tMRI) of Small Changes in the $T_1$ and Spatial Properties of Normal or Near Normal Appearing White and Gray Matter in Disease of the Brain using Divided Subtracted Inversion Recovery (dSIR) and Divided Reverse Subtracted Inversion Recovery (drSIR) Sequences. Quant Imaging Med Surg 2023 13(10):7304-7337.
3. Marques J P, Kober T, Krueger G, van der Zwaag W, Van de Moortele P-F, Gruetter R. MP2RAGE, a self bias-field corrected sequence for improved segmentation and $T_1$-mapping at high field. Neuroimage 2010; 49(2):1271-81.
4. Beaumont J, Saint-Jalmes H, Acosta O, Kober T, Tanner M, Ferre J C, Salvado O, Fripp J, Gambarota G. Multi $T_1$-weighted contrast MRI with fluid and white matter suppression at 1.5T. Magn Reson Imaging 2019; 63:217-225.
5. Beaumont J, Gambarota G, Saint-Jalmes H, Acosta O, Ferre J-C, Raniga P, Fripp J. High-resolution multi-$T_1$-weighted contrast and $T_1$ mapping with low $B_1$+sensitivity using the fluid and white matter suppression (FLAWS) sequence at 7T. Magn Reson Med 2021; 85(3):1364-1378.
6. Ferreira V M, Wijesurendra R S, Liu A, Greiser A, Casadei B, Robson M D, et al. Systolic shMOLLI myocardial $T_1$-mapping for improved robustness to partial-volume effects and applications in tachyarrhythmias. J Cardiovasc Magn Reson 2015; 17(1):77.

7. Wei Z, Jang H, Bydder G M, Yang W, Ma Y-J. Fast T1 measurement of cortical bone using 3D UTE actual flip angle imaging and single-T R acquisition (3d UTE-AFI-STR). Magn Reson Med 2021; 85(6):3290-3298.
8. Ma D, Gulani V, Seiberlich N, Liu K, Sunshine J L, Duerk J L, et al. Magnetic resonance fingerprinting. Nature 2013; 495(7440):187-192.
9. Young I R, Szeverenyi N M, Du J, Bydder G M. Pulse sequences as tissue property filters (T P filters): a way of understanding the signal, contrast and weighting of magnetic resonance images. Quant Imaging Med Surg. 2020; 10(5):1080-1120.
10. Ma Y-J, Fan S, Shao H, Du J, Szeverenyi N M, Young I R, Bydder G M. Use of Multiplied, Added, Subtracted and/or fiTted Inversion Recovery (MASTIR) pulse sequences. Quant Imaging Med Surg 2020; 10(6):1334-1369.
11. Ma Y J, Shao H, Fan S, Lu X, Du J, Young I R, et al. New options for increasing the sensitivity, specificity and scope of synergistic contrast magnetic resonance imaging (scMRI) using Multiplied, Added, Subtracted and/or FiTted (MASTIR) pulse sequences. Quant Imaging Med Surg. 2020; 10(10):2030-2065.

The invention claimed is:

1. A method for generating a magnetic resonance image, comprising:

acquiring a first inversion recovery signal using a first inversion time;

acquiring a second inversion recovery signal using a second inversion time;

performing mathematical operations on the first inversion recovery signal and the second inversion recovery signal by applying Bloch equations to generate a plurality of synthetic divided subtracted inversion recovery (dSIR) or synthetic BipoLAr Inversion Recovery (BLAIR) image data sets with a plurality of different inversion times, wherein the Bloch equations are used to generate the plurality of synthetic dSIR or synthetic BLAIR image data sets;

generating synthetic dSIR images based on the plurality of synthetic dSIR or synthetic BLAIR image data sets; and generating synthetic reversed dSIR (drSIR) images based on the plurality of synthetic dSIR or synthetic BLAIR image data sets.

2. The method of claim 1, further comprising:

generating a T1 map based on one of the synthetic dSIR image data sets within its middle domain (mD) from the plurality of synthetic dSIR image data sets; and using a phase difference between the inversion recovery signals to disambiguate T1 maps outside the mD of the plurality of synthetic dSIR image data sets.

3. The method of claim 2, wherein generating the synthetic dSIR image comprises:

generating the synthetic dSIR image from the T1 map by applying a bipolar filter to generate high-contrast images from the T1 map free of signal saturation at selected signal levels; and using a tissue property map to generate the synthetic dSIR image or the synthetic drSIR image with freely selected inversion times.

4. The method of claim 1, wherein performing the mathematical operations includes:

generating a logarithm of subtracted inversion recovery (lSIR) images produced from two inversion recovery images with different inversion times;

using an inverse hyperbolic tangent on the plurality of synthetic dSIR image data sets to generate a logarithm of the subtracted inversion recovery (lSIR) images; and using T1 tissue property maps to generate synthetic lSIR images with a plurality of different inversion times.

5. The method of claim 1, wherein one or more of the plurality of synthetic dSIR image data sets exhibits whiteout, grayout, or bubble signs.

6. The method of claim 1, wherein synthetic BLAIR images with a plurality of inversion times are produced using Bloch equations from (i) the two inversion recovery images from directly acquired dSIR or drSIR images, and/or from (ii) T1 maps and/or other tissue property maps.

7. A method of generating a magnetic resonance image, comprising:

obtaining at least one of a T1 map, T2 map, T2* map, perfusion map or D* map of a subject; and applying a bipolar filter to the at least one obtained map to create a plurality of synthetic BipoLAr Inversion Recovery (BLAIR) images with a plurality of different inversion times, wherein creating the plurality of synthetic BLAIR images includes applying one or more signal models derived from Bloch equations to the at least one obtained map.

8. The method of claim 7, further comprising providing a gadolinium-based contrast agent or magnetic iron oxide particles to the subject.

9. The method of claim 7, wherein the plurality of synthetic BLAIR images with the plurality of different inversion times exhibit increased sensitivity to paramagnetic effects of molecular oxygen.

10. The method of claim 7, wherein the at least one of the T1 map, T2 map, T2* map, perfusion map or D* map is used with manipulation of blood longitudinal magnetization by slice-selected and non-slice-selected inversion pulses to visualize blood flow and/or perfusion.

11. The method of claim 7, wherein the plurality of synthetic BLAIR images with the plurality of different inversion times are used to demonstrate signal changes or T1 changes induced by intentional or incidental Magnetization Transfer (MT) pulses.

12. The method of claim 7, further comprising applying a bipolar filter to a phase map to amplify contrast in selected tissue property domains of the subject.

13. The method of claim 7, wherein one or more of the plurality of synthetic BLAIR images exhibit whiteout, grayout, or bubble signs.

14. The method of claim 7, further comprising mathematically combining two or more images of the plurality of synthetic BLAIR images to generate another image with different contrast.

15. A method of generating a functional magnetic resonance imaging (fMRI) image, comprising:

acquiring a series of synthetic divided subtracted inversion recovery (dSIR) images with T2* sensitization during a functional task, wherein the series of synthetic dSIR images is synthetically generated using Bloch equations and has a plurality of different inversion times;

analyzing the series of synthetic dSIR images to identify a region of signal change corresponding to brain activation; and generating at least one synthetic fMRI image corresponding to the identified region of signal change, wherein the at least one synthetic fMRI image exhibits increased sensitivity to both perfusion and Blood Oxygen Level Dependent (BOLD) effects.

16. A method for generating bipolar filter magnetic resonance images using Multiplied, Added, Subtracted and/or Divided Echo Acquisition (MASDEA) sequences, including:

acquiring at least two echo acquisition signals;

performing mathematical operations using Bloch equations on the at least two echo acquisition signals, wherein performing mathematical operations includes at least one of multiplication, addition, subtraction, and division, and wherein performing the mathematical operations includes applying one or more signal models derived from the Bloch equations to the at least two echo acquisition signals; and generating a synthetic image data set based on the performed mathematical operations to visualize iron-containing tissues with increased sensitivity.

* * * * *